United States Patent
Yao et al.

(10) Patent No.: US 12,209,124 B2
(45) Date of Patent: Jan. 28, 2025

(54) ANTI-IL-17A ANTIBODY AND USE THEREOF

(71) Applicants: Shanghai Junshi Biosciences Co., Ltd., Shanghai (CN); Suzhou Junmeng Biosciences Co., Ltd., Suzhou (CN)

(72) Inventors: Jian Yao, Suzhou (CN); Dan Meng, Suzhou (CN); Hui Feng, Suzhou (CN); Sheng Yao, Suzhou (CN); Hai Wu, Suzhou (CN)

(73) Assignees: Shanghai Junshi Biosciences Co., Ltd., Shanghai (CN); Suzhou Junmeng Biosciences Co., Ltd., Suzhou (CN)

( * ) Notice: Subject to any disclaimer, the term of this patent is extended or adjusted under 35 U.S.C. 154(b) by 889 days.

(21) Appl. No.: 17/413,152

(22) PCT Filed: Dec. 11, 2019

(86) PCT No.: PCT/CN2019/124486
§ 371 (c)(1),
(2) Date: Jun. 11, 2021

(87) PCT Pub. No.: WO2020/119707
PCT Pub. Date: Jun. 18, 2020

(65) Prior Publication Data
US 2023/0159632 A1 May 25, 2023

(30) Foreign Application Priority Data
Dec. 12, 2018 (CN) .......................... 201811515045.7

(51) Int. Cl.
*C07K 16/24* (2006.01)
*A61P 37/02* (2006.01)
*C12N 15/63* (2006.01)

(52) U.S. Cl.
CPC ............ *C07K 16/244* (2013.01); *A61P 37/02* (2018.01); *C12N 15/63* (2013.01); *C07K 2317/24* (2013.01); *C07K 2317/565* (2013.01)

(58) Field of Classification Search
CPC .............. C07K 16/244; C07K 2317/24; C07K 2317/565; C07K 2317/56; C07K 2317/76; C07K 16/24; C07K 2317/92; C07K 2319/30; A61P 37/02; A61P 11/00; A61P 11/06; A61P 13/12; A61P 17/06; A61P 19/02; A61P 19/08; A61P 25/00; A61P 29/00; A61P 35/00; C12N 15/63; A61K 2039/505; A61K 39/395
See application file for complete search history.

(56) References Cited

U.S. PATENT DOCUMENTS

2011/0236390 A1* 9/2011 Almagro ................. A61P 17/00
424/139.1

FOREIGN PATENT DOCUMENTS

| CN | 105073775 A | 11/2015 |
|---|---|---|
| CN | 106336459 A | 1/2017 |
| CN | 106474470 A | 3/2017 |
| CN | 107522783 A | 12/2017 |
| CN | 107556382 A | 1/2018 |
| JP | 2009540824 A | 11/2009 |
| JP | 2010500028 A | 1/2010 |
| JP | 2016208508 A | 12/2016 |
| JP | 2017502924 A | 1/2017 |
| RU | 2577228 C2 | 3/2016 |
| WO | 2007149032 A1 | 12/2007 |
| WO | 2008021156 A2 | 2/2008 |
| WO | 2014122613 A1 | 8/2014 |
| WO | 2015070697 A1 | 5/2015 |
| WO | 2016103153 A1 | 6/2016 |
| WO | 2017215524 A1 | 12/2017 |
| WO | 2018050028 A1 | 3/2018 |

OTHER PUBLICATIONS

Sela-Culang, et al., Front. in Immunol. 2013; vol. 4 Article 302 (Year: 2013).*
PCT/CN2019/124486, "International Search Report (with Translation) and Written Opinion", Feb. 24, 2020, 13 pages.
Sun et al., "Preparation of a Neutralizing Monoclonal Antibody to Human IL-17", Immunological Journal, Jul. 31, 2011, pp. 607-609, sections 1-2, vol. vol. 28.
Toussirot et al. "Ixekizumab: an anti-IL-17 A monoclonal antibody for the treatment of psoriatic arthritis", Expert Opinion on Biological Therapy, Nov. 29, 2017, pp. 1-7.
Application No. EP19897274.7, Extended European Search Report, Mailed on Aug. 9, 2022, 10 pages.
Gaffen et al., "The IL-23-IL-17 Immune Axis: from Mechanisms to Therapeutic Testing", Nature Reviews Immunology, vol. 14, No. 9, Sep. 2014, pp. 585-600.
Gerhardt et al., Structure of IL-17A in Complex with a Potent, Fully Human Neutralizing Antibody, Journal of Molecular Biology, vol. 394, No. 5, Dec. 18, 2009, pp. 905-921.

(Continued)

*Primary Examiner* — Julie Wu
*Assistant Examiner* — Sydney Van Druff
(74) *Attorney, Agent, or Firm* — Kilpatrick Townsend & Stockton LLP

(57) ABSTRACT

The present invention provides an antibody or a functional fragment thereof that specifically binds to IL-17A with high affinity. Also provided are a nucleic acid molecule encoding the antibody or the functional fragment thereof disclosed herein, an expression vector and a host cell for expressing the antibody or the functional fragment thereof disclosed herein, and a method for preparing the antibody or the functional fragment thereof disclosed herein. The present invention also provides a pharmaceutical composition comprising the antibody or the functional fragment thereof disclosed herein, and use of the antibody or the functional fragment thereof disclosed herein for treating an immune dysfunction disease.

15 Claims, 8 Drawing Sheets
Specification includes a Sequence Listing.

(56) References Cited

OTHER PUBLICATIONS

Mease et al., Ixekizumab, an interleukin-17A specific monoclonal antibody, for the treatment of biologic-naive patients with active psoriatic arthritis: results from the 24-week randomised, double-blind, placebo-controlled and active (adalimumab)-controlled period of th, Annals of the Rheumatic Diseases, vol. 76, No. 1, Sep. 6, 2016, 9 pages.

* cited by examiner

SEQUENCE LISTING

```
<160> NUMBER OF SEQ ID NOS: 69

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR1

<400> SEQUENCE: 1

Gly Tyr Ile Phe Thr Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: HCDR2

<400> SEQUENCE: 2

Ile Asn Asp His Thr Gly Glu Pro
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR3

<400> SEQUENCE: 3

Ala Asn Tyr Gly Phe Gly Tyr Phe Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR1

<400> SEQUENCE: 4

Asn Tyr Asp Ile His
1               5

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR2

<400> SEQUENCE: 5

Val Ile Trp Ala Gly Gly Arg Thr His Ser Asp Ser Ala Leu Met Ser
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR3

<400> SEQUENCE: 6

Glu Gly Gly Asp Tyr Tyr Lys Tyr Leu Asp Phe
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: HCDR1

<400> SEQUENCE: 7

Asp Thr Tyr Ile His
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR2

<400> SEQUENCE: 8

Arg Ile Asp Pro Ala Asn Gly Asn Thr Lys Tyr Asp Pro Lys Phe Gln
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR3

<400> SEQUENCE: 9

Asp Tyr Tyr Gly Ser Ser Leu Leu Asp Tyr
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR1

<400> SEQUENCE: 10

Ser Asp Tyr Ala Trp
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR2

<400> SEQUENCE: 11

Phe Ile Ser Tyr Ser Gly Pro Thr Ser Tyr Asn Pro Ser Leu Lys Ser
1               5                   10                  15

<210> SEQ ID NO 12
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: HCDR3

<400> SEQUENCE: 12

Gly Gly Asp Gly Asp Ser Phe Asp Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR1

<400> SEQUENCE: 13

Gln Ser Leu Val His Ser Asn Gly Asn Ser Tyr
1               5                   10

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2

<400> SEQUENCE: 14

Lys Val Ser
1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR3

<400> SEQUENCE: 15

Ser Gln Ser Thr His Val Pro Tyr Thr
1               5

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR1

<400> SEQUENCE: 16

Arg Ser Gly Gln Ser Leu Val His Ser Asn Gly His Thr Tyr Phe His
1               5                   10                  15

<210> SEQ ID NO 17
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2

<400> SEQUENCE: 17

Lys Val Ser Asn Arg Phe Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR3

<400> SEQUENCE: 18

Ser Gln Ser Thr His Val Pro Tyr Thr
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR1

<400> SEQUENCE: 19

Lys Ala Ser His Asp Ile Asn Ser Tyr Leu Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2

<400> SEQUENCE: 20

Arg Ala Asn Gly Leu Val Asp
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR3

<400> SEQUENCE: 21

Leu Gln Tyr Glu Met Leu Pro Leu Thr
1               5

<210> SEQ ID NO 22
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR1

<400> SEQUENCE: 22

Arg Ser Ser Gln Ser Ile Val His Ser Asn Gly Asn Thr Tyr Leu Asp
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2

<400> SEQUENCE: 23

Lys Val Ser Asn Arg Phe Ser
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR3

<400> SEQUENCE: 24

Phe Gln Gly Ser His Phe Pro Thr
1               5

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 25

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Met Lys Gln Ala Pro Gly Lys Gly Leu Lys Trp Met
        35                  40                  45

Gly Trp Ile Asn Asp His Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Lys Glu Asp Thr Ala Thr Tyr Phe Cys
                85                  90                  95

Ala Asn Tyr Gly Phe Gly Tyr Phe Asp Tyr Trp Gly Gln Gly Thr Thr
            100                 105                 110
```

Leu Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 26

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Asn Tyr
            20                  25                  30

Asp Ile His Trp Leu Arg Gln Pro Pro Gly Lys Gly Leu Glu Trp Leu
        35                  40                  45

Gly Val Ile Trp Ala Gly Gly Arg Thr His Ser Asp Ser Ala Leu Met
    50                  55                  60

Ser Arg Leu Ser Ile Ser Lys Asp Asn Ser Lys Ser Gln Val Phe Leu
65                  70                  75                  80

Asn Val His Ser Leu Arg Pro Glu Asp Thr Ala Ile Tyr Tyr Cys Ala
                85                  90                  95

Arg Glu Gly Gly Asp Tyr Tyr Lys Tyr Leu Asp Phe Trp Gly Gln Gly
            100                 105                 110

Thr Thr Leu Thr Val Ser Ser
        115

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 27

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Gly Asp Lys Ser Ser Asn Ala Ala Tyr
65                  70                  75                  80

Leu Gln Leu Ser Arg Leu Thr Ser Glu Asp Thr Ala Val Tyr Tyr Cys
                85                  90                  95

Val Thr Asp Tyr Tyr Gly Ser Ser Leu Leu Asp Tyr Trp Gly Gln Gly
            100                 105                 110

Thr Thr Leu Thr Val Ser Ser
        115

<210> SEQ ID NO 28

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 28

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Ser Trp Ile Arg Gln Phe Pro Gly Asn Lys Leu Glu Trp
        35                  40                  45

Met Ala Phe Ile Ser Tyr Ser Gly Pro Thr Ser Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Lys Ser Val Thr Thr Glu Asp Thr Ala Thr Tyr Tyr Cys
                85                  90                  95

Ala Arg Gly Gly Asp Gly Asp Ser Phe Asp Tyr Trp Gly Gln Gly Thr
            100                 105                 110

Thr Leu Thr Val Ser Ser
        115

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL

<400> SEQUENCE: 29

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Ser Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL
```

<400> SEQUENCE: 30

Asp Val Val Thr Gln Thr Pro Leu Ser Leu Pro Val Ser Leu Gly
1               5                   10                  15

Asp Gln Ala Ser Ile Ser Cys Arg Ser Gly Gln Ser Leu Val His Ser
            20                  25                  30

Asn Gly His Thr Tyr Phe His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL

<400> SEQUENCE: 31

Asp Val Lys Met Thr Gln Ser Pro Ser Ser Met Tyr Ala Ser Leu Gly
1               5                   10                  15

Glu Arg Val Thr Ile Thr Cys Lys Ala Ser His Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Gly Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Val Tyr Tyr Cys Leu Gln Tyr Glu Met Leu Pro Leu
                85                  90                  95

Thr Phe Gly Ala Gly Thr Lys Leu Glu Leu Lys
            100                 105

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL

<400> SEQUENCE: 32

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
            50                  55                  60

Asp Arg Phe Ser Gly Ser Gly Ser Gly Thr Ser Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Thr Phe Gly Gly Gly Thr Lys Leu Glu Ile Lys
            100                 105                 110

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
                20                  25                  30

Gly Met Asn Trp Met Arg Gln Ala Pro Gly Gln Gly Leu Glu Trp Met
            35                  40                  45

Gly Trp Ile Asn Asp His Thr Gly Glu Pro Thr Tyr Ala Asp Lys Phe
        50                  55                  60

Gln Gly Arg Val Thr Phe Thr Leu Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Phe Gly Tyr Phe Asp Tyr Trp Gly Gln Gly Thr Leu
            100                 105                 110

Val Thr Val Ser Ser
        115

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL

<400> SEQUENCE: 34

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Gly Asn Ser Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser

```
                    85                  90                  95

Thr His Val Pro Tyr Thr Phe Gly Gln Gly Thr Lys Leu Glu Ile Lys
            100                 105                 110

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 35

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Ile Phe Thr Asn Tyr
                20                  25                  30

Gly Met Asn Trp Met Arg Gln Ala Pro Gly Gln Gly Leu Glu Trp Met
            35                  40                  45

Gly Trp Ile Asn Asp His Thr Gly Glu Pro Thr Tyr Ala Asp Lys Phe
    50                  55                  60

Gln Gly Arg Val Thr Phe Thr Leu Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Phe Gly Tyr Phe Asp Tyr Trp Gly Gln Gly Thr Leu
            100                 105                 110

Val Thr Val Ser Ser
        115

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL

<400> SEQUENCE: 36

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Gly Asn Ser Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 37
<211> LENGTH: 118
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Ile Ser Ser Asp
            20                  25                  30

Tyr Ala Trp Ser Trp Ile Arg Gln Pro Pro Gly Lys Gly Leu Glu Trp
        35                  40                  45

Ile Gly Phe Ile Ser Tyr Ser Gly Pro Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Asp Gly Asp Ser Phe Asp Tyr Trp Gly Gln Gly Thr
            100                 105                 110

Leu Val Thr Val Ser Ser
        115

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL

<400> SEQUENCE: 38

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Lys Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Thr Phe Gly Gln Gly Thr Lys Leu Glu Ile Lys
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL
```

```
<400> SEQUENCE: 39

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Ser Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Thr Phe Gly Gln Gly Thr Lys Leu Glu Ile Lys
            100                 105                 110

<210> SEQ ID NO 40
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln Pro Pro Gly Lys Gly Leu Glu Trp
        35                  40                  45

Ile Gly Phe Ile Ser Tyr Ser Gly Pro Thr Ser Tyr Asn Pro Ser Leu
    50                  55                  60

Lys Ser Arg Val Thr Ile Ser Arg Asp Thr Ser Lys Asn Gln Phe Phe
65                  70                  75                  80

Leu Gln Leu Lys Ser Val Thr Ala Ala Asp Thr Ala Val Tyr Tyr Cys
                85                  90                  95

Ala Arg Gly Gly Asp Gly Asp Ser Phe Asp Tyr Trp Gly Gln Gly Thr
            100                 105                 110

Thr Val Thr Val Ser Ser
        115

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL

<400> SEQUENCE: 41

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Ile Val His Ser
            20                  25                  30
```

```
Asn Gly Asn Thr Tyr Leu Asp Trp Tyr Leu Gln Lys Pro Gly Gln Ser
            35                  40                  45

Pro Lys Leu Leu Ile Tyr Lys Val Ser Asn Arg Phe Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Phe Pro Thr Phe Gly Gly Gly Thr Lys Val Glu Ile Lys
                100                 105                 110
```

<210> SEQ ID NO 42
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC

<400> SEQUENCE: 42

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Thr Asn Tyr
                 20                  25                  30

Gly Met Asn Trp Met Arg Gln Ala Pro Gly Gln Gly Leu Glu Trp Met
             35                  40                  45

Gly Trp Ile Asn Asp His Thr Gly Glu Pro Thr Tyr Ala Asp Lys Phe
 50                  55                  60

Gln Gly Arg Val Thr Phe Thr Leu Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Asn Tyr Gly Phe Gly Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270
```

```
Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 43
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC

<400> SEQUENCE: 43

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Ser Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 44
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC

<400> SEQUENCE: 44

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Ile Phe Thr Asn Tyr
            20                  25                  30

Gly Met Asn Trp Met Arg Gln Ala Pro Gly Gln Gly Leu Glu Trp Met
        35                  40                  45

Gly Trp Ile Asn Asp His Thr Gly Glu Pro Thr Tyr Ala Asp Lys Phe
    50                  55                  60

Gln Gly Arg Val Thr Phe Thr Leu Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Phe Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440
```

<210> SEQ ID NO 45
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC

<400> SEQUENCE: 45

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Ser Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210                 215

<210> SEQ ID NO 46
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Ile Ser Ser Asp
            20                  25                  30

Tyr Ala Trp Ser Trp Ile Arg Gln Pro Pro Gly Lys Gly Leu Glu Trp
        35                  40                  45

Ile Gly Phe Ile Ser Tyr Ser Gly Pro Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Asp Gly Asp Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

```
Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 47
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC

<400> SEQUENCE: 47

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Lys Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 48
<211> LENGTH: 218
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC

<400> SEQUENCE: 48

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Ser Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 49
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln Pro Pro Gly Lys Gly Leu Glu Trp
        35                  40                  45

Ile Gly Phe Ile Ser Tyr Ser Gly Pro Thr Tyr Asn Pro Ser Leu
    50                  55                  60

Lys Ser Arg Val Thr Ile Ser Arg Asp Thr Ser Lys Asn Gln Phe Phe
65                  70                  75                  80
```

Leu Gln Leu Lys Ser Val Thr Ala Ala Asp Thr Ala Val Tyr Tyr Cys
             85                  90                  95

Ala Arg Gly Gly Asp Gly Asp Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 50
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: LC

<400> SEQUENCE: 50

```
Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Phe Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 51
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: HC

<400> SEQUENCE: 51

```
caggtgcagc tggtgcagag cggcgccgag gtgaagaagc ccggcgccag cgtgaaggtg      60
agctgcaagg ccagcggcta catcttcacc aactacggca tgaactggat gagacaggcc     120
cccggccagg gcctggagtg gatgggctgg atcaacgacc acaccggcga gcccacctac     180
gccgacaagt tccagggcag agtgaccttc accctggaca ccagcatcag caccgcctac     240
atggagctga gcagactgag aagcgacgac accgccgtgt actactgcgc caactacggc     300
ttcggctact cgactactg gggccagggc accctggtga ccgtgagcag cgctagcacc     360
aagggcccca gcgtgttccc cctggcccct tgcagcagaa gcaccagcga gagcacagcc     420
gccctgggct gcctggtgaa ggactacttc cccgagcccg tgaccgtgtc ctggaacagc     480
ggcgctctga ccagcggcgt gcataccttc cccgccgtgc tccagagcag cggactgtac     540
tccctgagca gcgtggtgac cgtgccttcc agcagcctgg gcaccaagac ctacacctgc     600
```

| | |
|---|---|
| aacgtggacc acaagcccag caacaccaag gtggacaaga gagtggagag caagtacggc | 660 |
| cctccctgcc ccccttgccc tgccccgag ttcctgggcg gacctagcgt gttcctgttc | 720 |
| ccccccaagc ccaaggacac cctgatgatc agcagaaccc ccgaggtgac ctgcgtggtg | 780 |
| gtggacgtgt cccaggagga ccccgaggtc cagtttaatt ggtacgtgga cggcgtggaa | 840 |
| gtgcataacg ccaagaccaa gcccagagag gagcagttca acagcaccta cagagtggtg | 900 |
| tccgtgctga ccgtgctgca ccaggactgg ctgaacggca aggaatacaa gtgcaaggtc | 960 |
| tccaacaagg gcctgcctag cagcatcgag aagaccatca gcaaggccaa gggccagcca | 1020 |
| cgggagcccc aggtctacac cctgccacct agccaagagg agatgaccaa gaaccaggtg | 1080 |
| tccctgacct gtctggtgaa aggcttctat cccagcgata tcgccgtgga gtgggagagc | 1140 |
| aacggccagc ccgagaacaa ctacaagacc acccccctg tgctggacag cgacggcagc | 1200 |
| ttcttcctgt actccagact gaccgtggac aagtccagat ggcaggaggg caacgtcttc | 1260 |
| agctgctccg tgatgcacga ggccctgcac aaccactaca cccagaagtc cctgagcctg | 1320 |
| agcctgggca agtga | 1335 |

<210> SEQ ID NO 52
<211> LENGTH: 660
<212> TYPE: DNA
<213> ORGANISM: Artificial Sequence
<220> FEATURE:
<223> OTHER INFORMATION: Description of Artificial Sequence: Synthetic
 polynucleotide
<220> FEATURE:
<223> OTHER INFORMATION: LC

<400> SEQUENCE: 52

| | |
|---|---|
| gacgtggtga tgacccagag cccccctgagc ctgcccgtga ccctgggcca gccgccagc | 60 |
| atcagctgca gaagcagcca gagcctggtg cacagcaacg gcaacagcta cctgcactgg | 120 |
| tacctgcaga agcccggcca gagccccag ctgctgatct acaaggtgag caacagattc | 180 |
| agcggcgtgc ccgacagatt cagcggcagc ggcagcggca ccgacttcac cctgaagatc | 240 |
| agcagagtgg aggccgagga cgtgggcgtg tactactgca gccagagcac ccacgtgccc | 300 |
| tacaccttcg gccagggcac caagctggag atcaagcgaa ctgtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct tcaacagggg agagtgttag | 660 |

<210> SEQ ID NO 53
<211> LENGTH: 1335
<212> TYPE: DNA
<213> ORGANISM: Artificial Sequence
<220> FEATURE:
<223> OTHER INFORMATION: Description of Artificial Sequence: Synthetic
 polynucleotide
<220> FEATURE:
<223> OTHER INFORMATION: HC

<400> SEQUENCE: 53

| | |
|---|---|
| cagatccagc tggtgcagag cggcgccgag gtgaagaagc ccggcgccag cgtgaagatc | 60 |
| agctgcaagg ccagcggcta catcttcacc aactacggca tgaactggat gagacaggcc | 120 |
| cccggccagg gcctggagtg gatgggctgg atcaacgacc acaccggcga gcccacctac | 180 |

```
gccgacaagt tccagggcag agtgaccttc accctggaca ccagcgccag caccgcctac    240
atggagctga gcagactgag aagcgacgac accgccgtgt actactgcgc caactacggc    300
ttcggctact tcgactactg gggccagggc accctggtga ccgtgagcag cgctagcacc    360
aagggcccca gcgtgttccc cctggcccct gcagcagaa gcaccagcga gagcacagcc     420
gccctgggct gcctggtgaa ggactacttc cccgagcccg tgaccgtgtc ctggaacagc    480
ggcgctctga ccagcggcgt gcataccttc cccgccgtgc tccagagcag cggactgtac    540
tccctgagca gcgtggtgac cgtgccttcc agcagcctgg gcaccaagac ctacacctgc    600
aacgtggacc acaagcccag caacaccaag gtggacaaga gagtggagag caagtacggc    660 cctcctgcc ccccttgccc tgccccgag ttcctgggcg acctagcgt gttcctgttc       720 cccccaagc caaggacac cctgatgatc agcagaaccc cgaggtgac ctgcgtggtg       780 gtggacgtgt cccaggagga ccccgaggtc cagtttaatt ggtacgtgga cggcgtggaa    840
gtgcataacg ccaagaccaa gcccagagag gagcagttca acagcaccta cagagtggtg    900
tccgtgctga ccgtgctgca ccaggactgg ctgaacggca aggaatacaa gtgcaaggtc    960
tccaacaagg gcctgcctag cagcatcgag aagaccatca gcaaggccaa gggccagcca   1020
cgggagcccc aggtctacac cctgccacct agccaagagg agatgaccaa gaaccaggtg   1080
tccctgacct gtctggtgaa aggcttctat cccagcgata tcgccgtgga gtgggagagc   1140
aacggccagc ccgagaacaa ctacaagacc ccccccctg tgctggacag cgacggcagc    1200
ttcttcctgt actccagact gaccgtggac aagtccagat ggcaggaggg caacgtcttc   1260
agctgctccg tgatgcacga ggccctgcac aaccactaca cccagaagtc cctgagcctg   1320
agcctgggca agtga                                                    1335

<210> SEQ ID NO 54
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: LC

<400> SEQUENCE: 54
gacgtggtga tgacccagag ccccctgagc ctgcccgtga ccctgggcca gccgccagc     60 atcagctgca gaagcagcca gagcctggtg cacagcaacg gcaacagcta cctgcactgg   120
tacctgcaga agcccggcca gagcccccag ctgctgatct acaaggtgag caacagattc   180
agcggcgtgc ccgacagatt cagcggcagc ggcagcggca ccgacttcac cctgaagatc   240
agcagagtgg aggccgagga cgtgggcgtg tacttctgca gccagagcac ccacgtgccc   300
tacaccttcg gccagggcac caagctggag atcaagcgaa ctgtggctgc caccatctgtc  360 ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 55
<211> LENGTH: 1338
```

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: HC

<400> SEQUENCE: 55

```
caggtgcagc tgcaggagag cggccccggc ctggtgaagc ccagcgagac cctgagcctg      60
acctgcaccg tgaccggcta cagcatcagc agcgactacg cctggagctg gatcagacag     120
ccccccggca agggcctgga gtggatcggc ttcatcagct acagcggccc caccagctac     180
aaccccagcc tgaagtccag agtgaccatc agcagagaca ccagcaagaa ccagttcagc     240
ctgaagctga gcagcgtgac cgccgccgac accgccgtgt actactgcgc cagaggcggc     300
gacggcgaca gcttcgacta ctggggccag ggcaccctgg tgaccgtgag cagcgctagc     360
accaagggcc ccagcgtgtt ccccctggcc ccttgcagca aagcaccag cgagagcaca      420 gccgccctgg gctgcctggt gaaggactac ttccccgagc ccgtgaccgt gtcctggaac     480
agcggcgctc tgaccagcgg cgtgcatacc ttccccgccg tgctccagag cagcggactg     540
tactccctga gcagcgtggt gaccgtgcct tccagcagcc tgggcaccaa gacctacacc     600
tgcaacgtgg accacaagcc cagcaacacc aaggtggaca agagagtgga gagcaagtac     660
ggccctccct gccccccttg ccctgccccc gagttcctgg gcggacctag cgtgttcctg     720 ttcccccca agcccaagga caccctgatg atcagcagaa cccccgaggt gacctgcgtg     780
gtggtggacg tgtcccagga ggaccccgag gtccagttta attggtacgt ggacggcgtg     840
gaagtgcata cgccaagac caagcccaga gaggagcagt tcaacagcac ctacagagtg     900
gtgtccgtgc tgaccgtgct gcaccaggac tggctgaacg gcaaggaata caagtgcaag     960
gtctccaaca agggcctgcc tagcagcatc gagaagacca tcagcaaggc caagggccag    1020
ccacgggagc cccaggtcta caccctgcca cctagccaag aggagatgac caagaaccag    1080
gtgtccctga cctgtctggt gaaaggcttc tatcccagcg atatcgccgt ggagtgggag    1140
agcaacggcc agcccgagaa caactacaag accacccccc ctgtgctgga cagcgacggc    1200
agcttcttcc tgtactccag actgaccgtg gacaagtcca gatggcagga gggcaacgtc    1260
ttcagctgct ccgtgatgca cgaggccctg cacaaccact acacccagaa gtccctgagc    1320
ctgagcctgg gcaagtga                                                  1338
```

<210> SEQ ID NO 56
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: LC

<400> SEQUENCE: 56

```
gacgtggtga tgacccagag ccccctgagc ctgcccgtga ccctgggcca gccgccagc      60 atcagctgca agagcagcca gagcatcgtg cacagcaacg gcaacaccta cctggactgg    120
tacctgcaga agccggcaa gagccccaag ctgctgatct acaaggtgag caacagattc    180
agcggcgtgc ccgacagatt cagcggcagc ggcagcggca ccgacttcac cctgaagatc    240
agcagagtgg aggccgagga cctgggcgtg tactactgct tccagggcag ccacttcccc    300
```

| | |
|---|---|
| accttcggcc agggcaccaa gctggagatc aagcgaactg tgctgcacc atctgtcttc | 360 |
| atcttcccgc catctgatga gcagttgaaa tctggaactg cctctgttgt gtgcctgctg | 420 |
| aataacttct atcccagaga ggccaaagta cagtggaagg tggataacgc cctccaatcg | 480 |
| ggtaactccc aggagagtgt cacagagcag gacagcaagg acagcaccta cagcctcagc | 540 |
| agcaccctga cgctgagcaa agcagactac gagaaacaca agtctacgc ctgcgaagtc | 600 |
| acccatcagg gcctgagctc gcccgtcaca aagagcttca caggggaga gtgttag | 657 |

```
<210> SEQ ID NO 57
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: LC

<400> SEQUENCE: 57
```

| | |
|---|---|
| gacgtggtga tgacccagag ccccctgagc ctgcccgtga ccctgggcca gcccgccagc | 60 |
| atcagctgca gaagcagcca gagcatcgtg cacagcaacg gcaacaccta cctggactgg | 120 |
| tacctgcaga gcccggcca gagccccaag ctgctgatct acaaggtgag caacagattc | 180 |
| agcggcgtgc ccgacagatt cagcggcagc ggcagcggca ccagcttcac cctgaagatc | 240 |
| agcagagtgg aggccgagga cctgggcgtg tactactgct ccagggcag ccacttcccc | 300 |
| accttcggcc agggcaccaa gctggagatc aagcgaactg tggctgcacc atctgtcttc | 360 |
| atcttcccgc catctgatga gcagttgaaa tctggaactg cctctgttgt gtgcctgctg | 420 |
| aataacttct atcccagaga ggccaaagta cagtggaagg tggataacgc cctccaatcg | 480 |
| ggtaactccc aggagagtgt cacagagcag gacagcaagg acagcaccta cagcctcagc | 540 |
| agcaccctga cgctgagcaa agcagactac gagaaacaca agtctacgc ctgcgaagtc | 600 |
| acccatcagg gcctgagctc gcccgtcaca aagagcttca caggggaga gtgttag | 657 |

```
<210> SEQ ID NO 58
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: HC

<400> SEQUENCE: 58
```

| | |
|---|---|
| caggtgcagc tgcaggagag cggcccggc ctggtgaagc ccagcgagac cctgagcctg | 60 |
| acctgcaccg tgagcggcta cagcatcacc agcgactacg cctggagctg gatcagacag | 120 |
| ccccccggca gggcctgga gtggatcggc ttcatcagct acagcggccc caccagctac | 180 |
| aaccccagcc tgaagtccag agtgaccatc agcagagaca ccagcaagaa ccagttcttc | 240 |
| ctgcagctga gtccgtgac cgccgccgac accgccgtgt actactgcgc cagaggcggc | 300 |
| gacggcgaca gcttcgacta ctggggccag ggcaccaccg tgaccgtgag cagcgctagc | 360 |
| accaagggcc ccagcgtgtt ccccctggcc ccttgcagca agagcaccag cgagagcaca | 420 |
| gccgccctgg gctgcctggt gaaggactac ttccccgagc ccgtgaccgt gtcctggaac | 480 |
| agcggcgctc tgaccagcgg cgtgcatacc ttccccgccg tgctccagag cagcggactg | 540 |
| tactccctga gcagcgtggt gaccgtgcct tccagcagcc tgggcaccaa gacctacacc | 600 |

```
tgcaacgtgg accacaagcc cagcaacacc aaggtggaca agagagtgga gagcaagtac      660
ggccctccct gccccccttg ccctgccccc gagttcctgg gcggacctag cgtgttcctg      720
ttccccccca gcccaagga caccctgatg atcagcagaa ccccgaggt gacctgcgtg        780 gtggtggacg tgtcccagga ggaccccgag gtccagttta attggtacgt ggacggcgtg     840
gaagtgcata cgccaagac caagcccaga gaggagcagt tcaacagcac ctacagagtg      900
gtgtccgtgc tgaccgtgct gcaccaggac tggctgaacg gcaaggaata caagtgcaag    960
gtctccaaca agggcctgcc tagcagcatc gagaagacca tcagcaaggc caagggccag    1020
ccacgggagc cccaggtcta caccctgcca cctagccaag aggagatgac caagaaccag    1080
gtgtccctga cctgtctggt gaaaggcttc tatcccagcg atatcgccgt ggagtgggag    1140
agcaacggcc agcccgagaa caactacaag accaccccc ctgtgctgga cagcgacggc    1200
agcttcttcc tgtactccag actgaccgtg gacaagtcca gatggcagga gggcaacgtc    1260
ttcagctgct ccgtgatgca cgaggccctg cacaaccact acacccagaa gtccctgagc    1320
ctgagcctgg gcaagtga                                                   1338
```

<210> SEQ ID NO 59
<211> LENGTH: 657
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: LC

<400> SEQUENCE: 59

```
gacgtggtga tgacccagac ccccctgagc ctgagcgtga cccccggcca gcccgccagc     60
atcagctgca agagcagcca gagcatcgtg cacagcaacg caacaccta cctggactgg    120 tacctgcaga agcccggcca gagccccaag ctgctgatct acaaggtgag caacagattc    180
agcggcgtgc ccgacagatt cagcggcagc ggcagcggca ccgacttcac cctgaagatc    240
agcagagtgg aggccgagga cgtgggcgtg tactactgct tccagggcag ccacttcccc   300
accttcggcg gcggcaccaa ggtggagatc aagcgaactg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgagctc gcccgtcaca aagagcttca acaggggaga gtgttag     657
```

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: HCDR1

<400> SEQUENCE: 60

Gly Tyr Ser Ile Thr Ser Asp Tyr Ala
1               5

```
<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR2

<400> SEQUENCE: 61

Ile Ser Tyr Ser Gly Pro Thr
1               5

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR3

<400> SEQUENCE: 62

Ala Arg Gly Gly Asp Gly Asp Ser Phe Asp Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR1

<400> SEQUENCE: 63

Gln Ser Ile Val His Ser Asn Gly Asn Thr Tyr
1               5                   10

<210> SEQ ID NO 64
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2

<400> SEQUENCE: 64

Lys Val Ser
1

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR3

<400> SEQUENCE: 65

Phe Gln Gly Ser His Phe Pro Thr
1               5
```

<210> SEQ ID NO 66
<211> LENGTH: 132
<212> TYPE: PRT
<213> ORGANISM: Homo sapiens

<400> SEQUENCE: 66

```
Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Asn Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
        115                 120                 125

His His Val Ala
    130
```

<210> SEQ ID NO 67
<211> LENGTH: 396
<212> TYPE: DNA
<213> ORGANISM: Homo sapiens

<400> SEQUENCE: 67

```
ggaatcacaa tcccacgaaa tccaggatgc ccaaattctg aggacaagaa cttccccggg    60
actgtgatgg tcaacctgaa catccataac cggaatacca ataccaatcc caaaaggtcc   120
tcagattact acaaccgatc cacctcacct tggaatctcc accgcaatga ggaccctgag   180
agatatccct ctgtgatctg gaggcaaagt gccgccacct gggctgcat caacgctgat    240 gggaacgtgg actaccacat gaactctgtc cccatccagc aagagatcct ggtcctgcgc   300
agggagcctc cacactgccc caactccttc cggctggaga agatactggt gtccgtgggc   360
tgcacctgtg tcaccccgat tgtccaccat gtggcc                             396
```

<210> SEQ ID NO 68
<211> LENGTH: 133
<212> TYPE: PRT
<213> ORGANISM: Homo sapiens

<400> SEQUENCE: 68

```
Arg Lys Ile Pro Lys Val Gly His Thr Phe Phe Gln Lys Pro Glu Ser
1               5                   10                  15

Cys Pro Pro Val Pro Gly Gly Ser Met Lys Leu Asp Ile Gly Ile Ile
            20                  25                  30

Asn Glu Asn Gln Arg Val Ser Met Ser Arg Asn Ile Glu Ser Arg Ser
        35                  40                  45

Thr Ser Pro Trp Asn Tyr Thr Val Thr Trp Asp Pro Asn Arg Tyr Pro
    50                  55                  60

Ser Glu Val Val Gln Ala Gln Cys Arg Asn Leu Gly Cys Ile Asn Ala
65                  70                  75                  80
```

Gln Gly Lys Glu Asp Ile Ser Met Asn Ser Val Pro Ile Gln Gln Glu
            85                  90                  95

Thr Leu Val Val Arg Arg Lys His Gln Gly Cys Ser Val Ser Phe Gln
        100                 105                 110

Leu Glu Lys Val Leu Val Thr Val Gly Cys Thr Cys Val Thr Pro Val
        115                 120                 125

Ile His His Val Gln
    130

<210> SEQ ID NO 69
<211> LENGTH: 2601
<212> TYPE: DNA
<213> ORGANISM: Homo sapiens

<400> SEQUENCE: 69

| | |
|---|---|
| atgggggccg cacgcagccc gccgtccgct gtcccggggc ccctgctggg gctgctcctg | 60 |
| ctgctcctgg gcgtgctggc cccggtggc gcctccctgc gactcctgga ccaccgggcg | 120 |
| ctggtctgct cccagccggg gctaaactgc acggtcaaga atagtacctg cctggatgac | 180 |
| agctggattc accctcgaaa cctgacccc tcctccccaa aggacctgca gatccagctg | 240 |
| cactttgccc acacccaaca aggagacctg ttccccgtgg ctcacatcga atggacactg | 300 |
| cagacagacg ccagcatcct gtacctcgag ggtgcagagt tatctgtcct gcagctgaac | 360 |
| accaatgaac gtttgtgcgt caggtttgag tttctgtcca aactgaggca tcaccacagg | 420 |
| cggtggcgtt ttaccttcag ccactttgtg gttgaccctg accaggaata tgaggtgacc | 480 |
| gttcaccacc tgcccaagcc catccctgat ggggacccaa accaccagtc aagaattttc | 540 |
| cttgtgcctg actgtgagca cgccaggatg aaggtaacca cgccatgcat gagctcaggc | 600 |
| agcctgtggg accccaacat caccgtggag accctggagg cccaccagct cgtgtgagc | 660 |
| ttcaccctgt ggaacgaatc tacccattac cagatcctgc tgaccagttt ccgcacatg | 720 |
| gagaaccaca gttgctttga gcacatgcac cacatacctg cgcccagacc agaagagttc | 780 |
| caccagcgat ccaacgtcac actcactcta cgcaacctta aggggtgctg tcgccaccaa | 840 |
| gtgcagatcc agcccttctt cagcagctgc ctcaatgact gcctcagaca ctccgcgact | 900 |
| gtttcctgcc cagaaatgcc agacactcca gaaccaattc cggactacat gcccctgtgg | 960 |
| gtgtactggt tcatcacggg catctccatc ctgctggtgg gctccgtcat cctgctcatc | 1020 |
| gtctgcatga cctggaggct agctgggcct ggaagtgaaa aatacagtga tgacaccaaa | 1080 |
| tacaccgatg gcctgcctgc ggctgacctg atcccccac cgctgaagcc caggaaggtc | 1140 |
| tggatcatct actcagccga ccacccctc tacgtggacg tggtcctgaa attcgcccag | 1200 |
| ttcctgctca ccgcctgcgg cacggaagtg gccctggacc tgctggaaga gcaggccatc | 1260 |
| tcggaggcag gagtcatgac ctgggtgggc cgtcagaagc aggagatggt ggagagcaac | 1320 |
| tctaagatca tcgtcctgtg ctcccgcggc acgcgcgcca gtggcaggc gctcctgggc | 1380 |
| cggggggcgc tgtgcggct cgctgcgac cacggaaagc ccgtggggga cctgttcact | 1440 |
| gcagccatga catgatcct cccggacttc aagaggccag cctgcttcgg cacctacgta | 1500 |
| gtctgctact tcagcgaggt cagctgtgac ggcgacgtcc ccgacctgtt cggcgcggcg | 1560 |
| ccgcggtacc cgctcatgga caggttcgag gaggtgtact ccgcatcca ggacctggag | 1620 |
| atgttccagc cggccgcat gcaccgcgta ggggagctgt cggggacaa ctacctgcgg | 1680 |
| agcccgggcg gcaggcagct ccgcgccgcc ctggacaggt tccgggactg gcaggtccgc | 1740 |

```
tgtcccgact ggttcgaatg tgagaacctc tactcagcag atgaccagga tgccccgtcc    1800
ctggacgaag aggtgtttga ggagccactg ctgcctccgg aaccggcat cgtgaagcgg     1860 gcgcccctgg tgcgcgagcc tggctcccag gcctgcctgg ccatagaccc gctggtcggg    1920
gaggaaggag gagcagcagt ggcaaagctg gaacctcacc tgcagcccg gggtcagcca     1980 gcgccgcagc ccctccacac cctggtgctc gccgcagagg aggggccct ggtggccgcg     2040 gtggagcctg ggcccctggc tgacggtgcc gcagtccggc tggcactggc ggggagggc     2100 gaggcctgcc cgctgctggg cagcccgggc gctgggcgaa atagcgtcct cttcctcccc    2160
gtggaccccg aggactcgcc ccttggcagc agcaccccca tggcgtctcc tgacctcctt    2220
ccagaggacg tgagggagca cctcgaaggc ttgatgctct cgctcttcga gcagagtctg    2280
agctgccagg cccaggggg ctgcagtaga cccgccatgg tcctcacaga cccacacacg     2340
ccctacgagg aggagcagcg gcagtcagtg cagtctgacc agggctacat ctccaggagc    2400
tccccgcagc cccccgaggg actcacggaa atggaggaag aggaggaaga ggagcaggac    2460
ccagggaagc cggccctgcc actctctccc gaggacctgg agagcctgag gagcctccag    2520
cggcagctgc ttttccgcca gctgcagaag aactcgggct gggacacgat ggggtcagag    2580
tcagaggggc ccagtgcatg a                                              2601
```

ANTI-IL-17A ANTIBODY AND USE THEREOF

CROSS REFERENCE

This application is a 371 application and claims the benefit of PCT Application No. PCT/CN2019/124486, filed Dec. 11, 2019, which claims benefit of CN Patent Application No. 201811515045.7, filed Dec. 12, 2018, which applications are incorporated herein by reference in their entirety.

REFERENCE TO A SEQUENCE LISTING

The Sequence Listing written in file Substitute_Sequence Listing_108587-1255674-000150US_SL.txt was created on Dec. 21, 2021, 72,905 bytes in size, is submitted electronically in ASCII format and is hereby incorporated by reference in its entirety for all purposes.

TECHNICAL FIELD

The present invention relates to an antibody and an antigen-binding fragment thereof that specifically bind to IL-17A. The present invention particularly relates to antibodies and antigen-binding fragments thereof that inhibit IL-17A-mediated bioactivity, and compositions containing the antibodies or antigen-binding fragments, and methods for the treatment of related diseases. The present invention more particularly relates to use of anti-IL-17A antibodies and antigen-binding fragments thereof in the treatment of immune pathological diseases, including autoimmune and inflammatory diseases such as rheumatoid arthritis, psoriasis, ankylosing spondylitis, multiple sclerosis, systemic lupus erythematosus (SLE), lupus nephritis, or chronic obstructive pulmonary disease, asthma, infectious granuloma, cystic fibrosis, or cancer.

BACKGROUND

Interleukin 17 (IL-17), also known as CTLA-8 or IL-17A, plays a key role in the immune system. The IL-17 family includes six members, i.e., IL-17A, IL-17B, IL-17C, IL-17D, IL-17E and IL-17F, all of which contain 4 highly conserved cysteine residues that are crucial. However, the biological effects of these members vary greatly. Among them, IL-17A and IL-17F have the most similar homology and biological functions, and are studied most deeply at present. IL-17A expressed in vivo has an N-terminal signal peptide consisting of 23 amino acids, which is cleaved to generate mature IL-17A. Mature IL-17A is disulfide-linked, and is typically secreted and present as a homodimer. Sometimes, it also binds to IL-17F to form a heterodimer IL-17AF. In general, IL-17A or IL-17 refers to IL-17A homodimer protein which is produced predominantly by helper T-cells 17 (T helper 17 or Th17), and may also be synthesized and secreted by other immune cells such as γδT cells, lymphoid tissue indicator (LTi) cells, innate lymphoid cells (ILCs) and natural killer T (NKT) cells (Cua D J, Tato C M., *Nature reviews*. 2010, 10:479-489). The regulation of IL-17A expression is very complicated. It was found that when cytokines such as IL-6, IL-1β and TGFβ induce initial CD4$^+$ T cells to differentiate into Th17, Th17 cells secrete a small amount of IL-17A due to their weak stability, and have weak tissue damage effect. IL-23, when present, causes an inflammatory outbreak and tissue damage by promoting the stability of Th17 cells for their continuous secretion of IL-17A, up-regulating the expression of pro-inflammatory factors (IL-22, CSF-2 and IFN-γ) and down-regulating the expression of anti-inflammatory factors (IL-2, IL-27 and IL-12) and other ways (McGeachy M J, et al., *Nature immunology*. 2009, 10:314-324). Therefore, the IL-17A pathway plays a critical role in tissue damage when IL-23 is abnormally expressed in tissues.

IL-17 is generally secreted at a specific site and acts in local tissues by binding to the IL-17 receptor (IL-17R) on the surface of target cells. The IL-17R family includes five members, that is IL-17RA, IL-17RB, IL-17RC, IL-17RD and IL-17RE, which are widely expressed on various cell membranes (Iwakura Y, et al., *Immunity*. 2011; 34:149-162). IL-17 mainly exerts effects by binding to IL-17RA/IL-17RC complex on the surface of cells of non-hematopoietic origin (such as epithelial cells and mesenchymal cells) (Ishigame H, et al., *Immunity*. 2009; 30:108-119), and damage tissues by promoting secretion of cytokines (such as IL-6, G-CSF, GM-CSF, IL-10, TGF-β and TNF-α), chemokines (including IL-8, CXCL1 and MCP-1), and prostaglandin (e.g., PGE2) by cells, inducing the aggregation of neutrophils and macrophages, and releasing reactive oxygen species (ROS) (Stark M A, et al., *Immunity*. 2005; 22:285-294). Autoimmune diseases, such as psoriasis, rheumatoid arthritis, ankylosing spondylitis, Crohn's disease and multiple sclerosis, pose a serious threat to human health. It was found that the dyssecretosis of IL-17 is closely related to the occurrence and development of such diseases. Antibodies targeting IL-17 are effective in alleviating symptoms of autoimmune diseases by inhibiting the IL-17-IL-17R signaling pathway (Sarah L, et al., *Nat Rev Immunol*. 2014, 14(9): 585-600). Cosentyx (secukinumab), developed by Novartis, is the first IL-17 monoclonal antibody in the world. Its approved indications include moderate to severe plaque psoriasis, providing an important first-line biological treatment option for the vast psoriasis population. However, it is urgent and significant to develop anti-IL-17 antibodies with different properties such as different structures, better efficacy and wider indication ranges for treating autoimmune-related disorders such as psoriasis, rheumatoid arthritis and ankylosing spondylitis as well as other IL-17-related diseases.

BRIEF SUMMARY

The present invention provides an antibody or an antigen-binding fragment thereof that specifically binds to human IL-17A, comprising at least one complementarity determining region (CDR) sequence selected from SEQ ID NOs: 1-24 and 60-65.

In one embodiment, the antibody or the antigen-binding fragment thereof disclosed herein comprises at least one heavy chain CDR domain selected from SEQ ID NOs: 1-3, 4-6, 7-9, 10-12 and 60-62, and/or at least one light chain CDR domain selected from SEQ ID NOs: 13-15, 16-18, 19-21, 22-24 and 63-65.

In one embodiment, the antibody or the antigen-binding fragment thereof disclosed herein comprises a heavy chain variable region (VH), wherein the VH comprises an HCDR1 selected from SEQ ID NOs: 1, 4, 7, 10 and 60, an HCDR2 selected from SEQ ID NOs: 2, 5, 8, 11 and 61, and an HCDR3 selected from SEQ ID NOs: 3, 6, 9, 12 and 62.

In one embodiment, the antibody or the antigen-binding fragment thereof disclosed herein comprises a heavy chain variable region (VH), wherein the VH comprises a set of HCDR1, HCDR2 and HCDR3 amino acid sequences selected from any of sets A to E:

| Set | HCDR1 | HCDR2 | HCDR3 |
| --- | --- | --- | --- |
| A | SEQ ID NO: 1 | SEQ ID NO: 2 | SEQ ID NO: 3 |
| B | SEQ ID NO: 4 | SEQ ID NO: 5 | SEQ ID NO: 6 |
| C | SEQ ID NO: 7 | SEQ ID NO: 8 | SEQ ID NO: 9 |
| D | SEQ ID NO: 10 | SEQ ID NO: 11 | SEQ ID NO: 12 |
| E | SEQ ID NO: 60 | SEQ ID NO: 61 | SEQ ID NO: 62 |

In one embodiment, the antibody or the antigen-binding fragment thereof disclosed herein comprises a light chain variable region (VL), wherein the VL comprises an LCDR selected from SEQ ID NOs: 13, 16, 19, 22 and 63, an LCDR2 selected from SEQ ID NOs: 14, 17, 20, 23 and 64, and an LCDR3 selected from SEQ ID NOs: 15, 18, 21, 24 and 65.

In one embodiment, the antibody or the antigen-binding fragment thereof disclosed herein comprises a light chain variable region (VL), wherein the VL comprises a set of LCDR1, LCDR2 and LCDR3 amino acid sequences selected from any of sets F to J:

| Set | LCDR1 | LCDR2 | LCDR3 |
| --- | --- | --- | --- |
| F | SEQ ID NO: 13 | SEQ ID NO: 14 | SEQ ID NO: 15 |
| G | SEQ ID NO: 16 | SEQ ID NO: 17 | SEQ ID NO: 18 |
| H | SEQ ID NO: 19 | SEQ ID NO: 20 | SEQ ID NO: 21 |
| I | SEQ ID NO: 22 | SEQ ID NO: 23 | SEQ ID NO: 24 |
| J | SEQ ID NO: 63 | SEQ ID NO: 64 | SEQ ID NO: 65 |

In one embodiment, the antibody or the antigen-binding fragment thereof disclosed herein comprises a heavy chain variable region (VH) and a light chain variable region (VL), wherein the variable regions comprise a set of 6 CDR amino acid sequences selected from any of sets I to VI:

| Set | HCDR1 | HCDR2 | HCDR3 | LCDR1 | LCDR2 | LCDR3 |
| --- | --- | --- | --- | --- | --- | --- |
| I | SEQ ID NO: 1 | SEQ ID NO: 2 | SEQ ID NO: 3 | SEQ ID NO: 13 | SEQ ID NO: 14 | SEQ ID NO: 15 |
| II | SEQ ID NO: 1 | SEQ ID NO: 2 | SEQ ID NO: 3 | SEQ ID NO: 16 | SEQ ID NO: 17 | SEQ ID NO: 18 |
| III | SEQ ID NO: 4 | SEQ ID NO: 5 | SEQ ID NO: 6 | SEQ ID NO: 19 | SEQ ID NO: 20 | SEQ ID NO: 21 |
| IV | SEQ ID NO: 7 | SEQ ID NO: 8 | SEQ ID NO: 9 | SEQ ID NO: 22 | SEQ ID NO: 23 | SEQ ID NO: 24 |
| V | SEQ ID NO: 10 | SEQ ID NO: 11 | SEQ ID NO: 12 | SEQ ID NO: 22 | SEQ ID NO: 23 | SEQ ID NO: 24 |
| VI | SEQ ID NO: 60 | SEQ ID NO: 61 | SEQ ID NO: 62 | SEQ ID NO: 63 | SEQ ID NO: 64 | SEQ ID NO: 65 |

In one embodiment, the antibody or the antigen-binding fragment thereof disclosed herein comprises a heavy chain variable region (VH) and/or a light chain variable region (VL), wherein the VH has an amino acid selected from SEQ ID NOs: 25, 26, 27, 28, 33, 35, 38 and 40, and/or the VL has an amino acid sequence selected from SEQ ID NOs: 29, 30, 31, 32, 34, 36, 38, 39 and 41.

In one embodiment, the antibody or the antigen-binding fragment thereof disclosed herein comprises a heavy chain variable region (VH) and a light chain variable region (VL), wherein the variable regions have a set of amino acid sequences selected from any of sets 1 to 7:

| Set | VH | VL |
| --- | --- | --- |
| 1 | SEQ ID NO: 25 | SEQ ID NO: 29 or 30 |
| 2 | SEQ ID NO: 26 | SEQ ID NO: 31 |
| 3 | SEQ ID NO: 27 or 28 | SEQ ID NO: 32 |
| 4 | SEQ ID NO: 33 or 35 | SEQ ID NO: 34 |
| 5 | SEQ ID NO: 35 | SEQ ID NO: 36 |
| 6 | SEQ ID NO: 37 | SEQ ID NO: 38 or 39 |
| 7 | SEQ ID NO: 40 | SEQ ID NO: 41 |

In one embodiment, the antibody or the antigen-binding fragment thereof disclosed herein comprises a light chain (LC) and/or a heavy chain (HC), wherein the HC has an amino acid sequence selected from SEQ ID NOs: 42, 44, 46 and 49, and/or the LC has an amino acid sequence selected from SEQ ID NOs: 43, 45, 47, 48 and 50.

In one embodiment, the antibody or the antigen-binding fragment thereof disclosed herein comprises a light chain (LC) and a heavy chain (HC), wherein the LC has an amino acid sequence set forth in SEQ ID NO: 43, and the HC has an amino acid sequence set forth in SEQ ID NO: 42 or 44; the LC has an amino acid sequence set forth in SEQ ID NO: 45, and the HC has an amino acid sequence set forth in SEQ ID NO: 44; the LC has an amino acid sequence set forth in SEQ ID NO. 47 or 48, and the HC has an amino acid sequence set forth in SEQ ID NO: 46; or the LC has an amino acid set forth in SEQ ID NO: 50, and the HC has an amino acid sequence set forth in SEQ ID NO: 49.

In one embodiment, the antibody disclosed herein is an intact antibody, preferably IgG, and more preferably IgG4.

In one specific embodiment, the antibody disclosed herein is 1F8, 2B2, 2F5, ch1, ch2, ch16, hu31, hu43, hu44, hu59, hu60 or hu250.

In one embodiment, the antibody or the antigen-binding fragment thereof disclosed herein is characterized by: a) specifically binding to IL-17A homodimer and IL-17AF heterodimer; b) blocking the binding of IL-17A to its receptor; and/or c) inhibiting IL-17A-mediated bioactivity.

In one embodiment, the IL-17A, IL-17AF or IL-17F described herein is selected from one or more of cynomolgus monkey, mouse and human.

In one embodiment, the antibody or the antigen-binding fragment thereof disclosed herein does not specifically bind to a) any one or more of human IL-17F homodimer, human IL-17B homodimer, human IL-17C homodimer, human IL-17D homodimer, and human IL-17E homodimer, and/or b) any one or more of cynomolgus monkey IL-17F homodimer and mouse IL-17F homodimer.

In another aspect, the antibody or the antigen-binding fragment thereof disclosed herein has the function of inhibiting the binding of IL-17A to its receptor, and/or reducing cell signal transduction and/or bioactivity mediated by IL-17A.

In one embodiment, the antibody or the antigen-binding protein thereof disclosed herein is capable of inhibiting IL-17A from inducing the secretion of CXCL1 by epithelial cells when assessed for activity in vitro.

In one embodiment, the antibody or the antigen-binding fragment thereof disclosed herein is capable of inhibiting IL-17A from inducing the secretion of CXCL1 in mice when assessed for activity in vivo.

In one embodiment, the antibody or the antigen-binding protein thereof disclosed herein is capable of resisting the onset of imiquimod-induced psoriasis in the mouse model, and reducing the clinical score of the psoriasis onset in mice and the degree of ear swelling of mice, when assessed for activity in vivo.

In one embodiment, the isolated antibody or the antigen-binding fragment thereof disclosed herein is capable of inhibiting knee joint swelling in antigen-induced arthritis models, such as cynomolgus monkey AIA-model, when assessed in vivo.

The present invention also provides the use of the antibody or the antigen-binding fragment thereof (preferably hu31, hu43, hu44, hu59, hu60 or hu250) as a medicament, preferably as a medicament for treating pathological diseases mediated by IL-17A and/or treated by inhibiting IL-17A signal transduction.

In one specific embodiment, the pathological disease mediated by IL-17A is an inflammatory disorder or condition, such as arthritis, rheumatoid arthritis, psoriasis, ankylosing spondylitis, chronic obstructive pulmonary disease, systemic lupus erythematosus (SLE), lupus nephritis, asthma, multiple sclerosis or cystic fibrosis.

The present invention provides a method for treating pathological diseases mediated by IL-17A, comprising administering an effective amount of the isolated antibody or the antigen-binding fragment thereof disclosed herein, preferably hu31, hu43, hu44, hu59, hu60, or hu250 antibody, so as to alleviate the condition.

The present invention also relates to a method for producing the antibody or the antigen-binding fragment thereof disclosed herein. Such methods include isolated nucleic acid molecules encoding at least the heavy and/or light chain variable region of an antibody or an protein disclosed herein, or a cloning/expression vector comprising such nucleic acids, particularly for recombinant in a host cell to produce the antibody or the protein disclosed herein, e.g., hu31, hu43, hu44, hu59, hu60 or hu250.

The present invention also relates to one or more cloning vectors and a host cell comprising the expression vectors, and a method for producing the antibody or the protein comprising the antigen-binding fragment thereof disclosed herein, specifically, such as hu31, hu43, hu44, hu59, hu60 or hu250 antibody, wherein the method comprises culturing the host cell, and purifying and isolating the antibody or the protein.

In one embodiment, the isolated antibody or the protein comprising an antigen-binding fragment thereof disclosed herein is conjugated to another active moiety.

In one embodiment, the antibody or the antigen-binding fragment thereof disclosed herein may be a monoclonal antibody or an antigen-binding fragment thereof, preferably a chimeric antibody, a humanized antibody or a human antibody or a portion thereof.

In one aspect of the present invention, provided is a pharmaceutical composition comprising the antibody or the protein comprising the antigen-binding fragment thereof according to any of the embodiments of the present invention, in combination with one or more pharmaceutically acceptable excipients, diluents or carriers.

In one embodiment, the pharmaceutical composition comprises one or more additional active ingredients.

In one specific embodiment, the pharmaceutical composition is a lyophilized powder. In another specific embodiment, the pharmaceutical composition is a stable liquid formulation comprising a therapeutically acceptable amount of the antibody or the molecule disclosed herein.

In one embodiment, the present invention relates to the use of the antibody or the antigen-binding fragment thereof for preparing a medicament for treating any one of the pathological disorders mediated by IL-17A.

The present invention provides an isolated nucleic acid molecule encoding the antibody or the antigen-binding fragment thereof, an expression vector or a recombinant vector comprising the nucleic acid molecule, and a host cell transformed with the vector.

The present invention provides a pharmaceutical composition comprising the antibody or the antigen-binding fragment thereof, the nucleic acid molecule, the vector or the host cell, and a pharmaceutically acceptable carrier or excipient.

The present invention provides the use of the antibody or the antigen-binding fragment thereof, the nucleic acid molecule, the vector or the host cell, or the pharmaceutical composition for preparing a medicament for treating and/or preventing diseases or disorders mediated by IL-17A.

In some embodiments, the medicament is a medicament for treating arthritis, rheumatoid arthritis, psoriasis, ankylosing spondylitis, chronic obstructive pulmonary disease, systemic lupus erythematosus (SLE), lupus nephritis, asthma, multiple sclerosis or cystic fibrosis.

DETAILED DESCRIPTION

Figure 1:
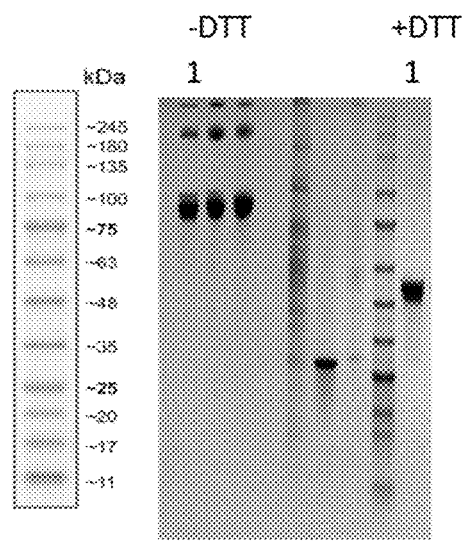
FIG. 1 shows the SDS-PAGE electropherogram of the recombinant human IL-17A-mFc protein.

The present invention relates to an antibody that specifically binds to human IL-17A and blocks IL-17A-mediated bioactivity. The present invention relates to a full-length IgG antibody and an antigen-binding fragment thereof, described further below.

Definitions

Unless otherwise stated, embodiments of the present invention will employ conventional techniques of molecular biology (including recombinant techniques), microbiology, cytobiology, biochemistry and immunology, which are all within the skill of the art.

In order to facilitate the understanding of the present invention, some technical and scientific terms are specifically defined as follows. Unless otherwise specifically defined herein, all technical and scientific terms used herein have the same meaning as commonly understood by those of ordinary skill in the art to which the present invention belongs. For definitions and terminology in the art, the skilled person can refer specifically to Current Protocolsin Molecular Biology (Ausubel). Abbreviations for amino acid residues are standard 3-letter and/or 1-letter codes used in the art to denote one of the 20 commonly used L-amino acids. The singular forms used herein (including claims) include their plural forms, unless otherwise specified in the context explicitly.

IL-17 or IL-17A is interleukin-17. Unless otherwise stated, the IL-17 usually refers to human IL-17A.

IL-17A expressed in vivo, its NCBI accession No. NP-443104.1, has an N-terminal signal peptide consisting of 23 amino acids, which is cleaved to generate mature IL-17A. In one specific embodiment, IL-17A disclosed herein refers to mature IL-17A, which does not comprise an N-terminal signal peptide, with an amino acid sequence set forth in SEQ ID NO: 66 and a nucleotide sequence set forth in SEQ ID NO: 67.

IL-17F expressed in vivo, its NCBI accession No. NP-443104.1, has an N-terminal signal peptide consisting of 30 amino acids, which is cleaved to generate mature IL-17F. In one specific embodiment, IL-17F disclosed herein refers to mature IL-17F, which does not comprise an N-terminal signal peptide, with an amino acid sequence set forth in SEQ ID NO: 68.

IL-17AF disclosed herein is a heterodimer of an IL-17A subunit and an IL-17F subunit, as understood by those of ordinary skill in the art.

The term "immune response" refers to the action of, for example, lymphocytes, antigen-presenting cells, phagocytes, granulocytes, and soluble macromolecules produced by the above cells or liver (including antibodies, cytokines, and complements) that results in selective damage to, destruction of, or elimination from the human body of invading pathogens, cells or tissues infected with pathogens, cancerous cells, or, in cases of autoimmunity or pathological inflammation, normal human cells or tissues.

The term "signal transduction pathway" or "signal transduction activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. The penultimate process typically involves a nuclear event, resulting in a change in gene expression.

With respect to the antibody or the antigen-binding fragment thereof disclosed herein, the term "activity" or "bioactivity", or the term "biological property" or "biological characteristic" can be used interchangeably herein and includes, but is not limited to, epitope/antigen affinity and specificity, the ability to neutralize or antagonize IL-17A activity in vivo or in vitro, $IC_{50}$, the in vivo stability of the antibody, and the immunogenic properties of the antibody. Other identifiable biological properties or characteristics of the antibody known in the art include, for example, cross-reactivity (i.e., cross-reactivity with non-human homologs of the targeted peptide, or with other proteins or tissues in general), and the ability to maintain high expression level of the protein in mammalian cells. The aforementioned properties or characteristics are observed, determined or assessed using techniques well known in the art, including but not limited to ELISA, FACS or BIACORE plasma resonance analysis, unlimited in vitro or in vivo neutralization assays, receptor binding, cytokine or growth factor production and/or secretion, signal transduction, and immunohistochemistry of tissue sections of different origins (including human, primate or any other origin).

An "antibody" refers to any form of antibody having a desired bioactivity. Thus, it is used in the broadest sense and specifically includes, but is not limited to, monoclonal antibodies (including full-length monoclonal antibodies), polyclonal antibodies, multispecific antibodies (e.g., bispecific antibodies), humanized antibodies, fully human antibodies, chimeric antibodies, and camelized single domain antibodies.

An "isolated antibody" refers to the purified state of a conjugate, and in this case means that the molecule is substantially free of other biomolecules, such as nucleic acids, proteins, lipids, sugars, or other substances such as cell debris and growth medium. The term "isolate(d)" does not mean the complete absence of such substances or the absence of water, buffers or salts, unless they are present in amounts that will significantly interfere with the experimental or therapeutic use of the conjugates described herein.

A "monoclonal antibody" refers to an antibody obtained from a substantially homogeneous population of antibodies, i.e., the antibodies comprising the population are identical except for possible naturally occurring mutations that may be present in minor amounts. A monoclonal antibody is highly specific and targets a single antigen epitope. In contrast, conventional (polyclonal) antibody preparations typically include a large number of antibodies targeting (or specific for) different epitopes. The modifier "monoclonal" indicates the characteristic of an antibody obtained from a substantially homogeneous population of antibodies, and is not to be construed as producing the antibody by any particular method.

A "full-length antibody" refers to an immunoglobulin molecule comprising four peptide chains when present naturally, including two heavy (H) chains (about 50-70 kDa in full length) and two light (L) chains (about 25 kDa in full length) linked to each other by disulfide bonds. Each heavy chain consists of a heavy chain variable region (abbreviated herein as VH) and a heavy chain constant region (abbreviated herein as CH). The heavy chain constant region consists of 3 domains CH1, CH2 and CH3. Each light chain consists of a light chain variable region (abbreviated herein as VL) and a light chain constant region. The light chain constant region consists of one domain CL. The VH and VL regions can be further divided into complementarity determining regions (CDRs) with high variability and more conservative regions called framework regions (FRs) that are spaced apart by the CDRs. Each VH or VL region consists of 3 CDRs and 4 FRs, in the following order from the amino terminus to the carboxyl terminus: FR1, CDR1, FR2, CDR2, FR3, CDR3, FR4. The variable regions of the heavy and light chains contain binding domains that interact with antigens. The constant regions of an antibody can mediate the binding of immunoglobulins to host tissues or factors, including the binding of various cells of the immune system (e.g., effector cells) to the first component (C1q) of classical complement system.

An "antigen-binding fragment" of an antibody ("parent antibody") includes a fragment or a derivative of the antibody, generally including at least one fragment of an antigen-binding region or variable region (e.g., one or more CDRs) of a parent antibody, which retains at least some of the binding specificity of the parent antibody. Examples of binding fragments of an antibody include, but are not limited to, Fab, Fab', F(ab')$_2$ and Fv fragments; a diabody; a linear antibody; a single-chain antibody molecule, such as sc-Fv; and a nanobody and a multispecific antibody formed by fragments of the antibody. A binding fragment or a derivative generally retains at least 10% of its antigen-binding activity when the antigen-binding activity is present on a molar concentration basis. Preferably, the binding fragment or derivative retains at least 20%, 50%, 70%, 80%, 90%, 95% or 100% or more of the antigen-binding affinity of the parent antibody. It is also contemplated that an antigen-binding fragment of an antibody may include conservative or non-conservative amino acid substitutions that do not significantly alter their bioactivity (referred to as "conservative variants" or "function-conservative variants" of the antibody). The term "conjugate" refers to both an antibody and a binding fragment thereof.

A "single chain Fv" or "scFv" antibody refers to an antibody fragment comprising the VH and VL domains of an antibody, where these domains are present in a single polypeptide chain. In general, an Fv polypeptide also comprises a polypeptide linker between the VH and VL domains that enables the scFv to form the desired structure for antigen-binding.

A "domain antibody" is an immunofunctional immunoglobulin fragment that contains only the variable region of the heavy chain or the light chain. In certain cases, two or more VH regions are covalently linked to a peptide linker to form a bivalent domain antibody. The 2 VH regions of the bivalent domain antibody may target the same or different antigens.

A "bivalent antibody" comprises 2 antigen-binding sites. In certain cases, the 2 binding sites have the same antigen specificity. However, a bivalent antibody may be bispecific.

A "diabody" refers to a small antibody fragment having two antigen-binding sites, which comprises a heavy chain variable domain (VH) linked to a light chain variable domain (VL) in the same polypeptide chain (VH-VL or VL-VH). By using a linker that is too short for pairing between two domains in one chain, the domains are forced to pair with the complementary domains of the other chain to form two antigen-binding sites.

A "chimeric antibody" is an antibody having the variable domains of a first antibody and the constant domains of a second antibody, wherein the first and second antibodies are from different species. Typically, the variable domain is obtained from an antibody of an experimental animal such as a rodent ("parent antibody"), and the constant domain sequence is obtained from a human antibody, such that the resulting chimeric antibody is less likely to induce an adverse immune response in a human subject as compared to the parent rodent antibody.

A "humanized antibody" refers to an antibody form containing sequences from both human and non-human (such as mouse and rat) antibodies. In general, a humanized antibody comprises substantially all of at least one, and typically two, variable domains, in which all or substantially all of the hypervariable loops correspond to those of a non-human immunoglobulin and all or substantially all of the framework regions (FRs) are those of a human immunoglobulin sequence. The humanized antibody may optionally comprise at least a portion of a human immunoglobulin constant region (Fc).

A "fully human antibody" refers to an antibody that comprises only human immunoglobulin sequences. A fully human antibody may contain mouse glycochains if produced in mice, mouse cells, or hybridomas derived from mouse cells. Likewise, a "mouse antibody" refers to an antibody that comprises only mouse immunoglobulin sequences.

Alternatively, a fully human antibody may contain rat glycochains if produced in rats, rat cells, or hybridomas derived from rat cells. Likewise, a "rat antibody" refers to an antibody that comprises only rat immunoglobulin sequences.

"Isotype" refers to the type of antibodies (e.g., IgM, IgE, IgG such as IgG1 or IgG4) provided by the heavy chain constant region genes. Isotype also includes modified forms of one of these types in which modifications have been made to alter Fc function, for example to enhance or attenuate effector function or binding to Fc receptors.

The term "nucleic acid" or "polynucleotide" refers to deoxyribonucleic acid (DNA) or ribonucleic acid (RNA) and polymers thereof in either single- or double-stranded form. Unless explicitly limited, the term encompasses nucleic acids containing known analogs of natural nucleotides that have similar binding properties as the reference nucleic acid and are metabolized in a manner similar to naturally occurring nucleotides. (see U.S. Pat. No. 8,278,036 to Kariko et al., which discloses an mRNA molecule where uridine is substituted by pseudouridine, a method for synthesizing the mRNA molecule, and a method for delivering therapeutic proteins in vivo). Methods of modified mRNA can be used, for example, those disclosed in U.S. Pat. No. 8,278,036 to Kariko et al. and in Patent Application No. WO2013/090186A1 to Moderna. Unless otherwise specified, a particular nucleic acid sequence also implicitly includes conservatively modified variants thereof (e.g., degenerate codon substitutions), alleles, orthologs, SNPs, and complementary sequences as well as the sequence explicitly indicated. Specifically, degenerate codon substitutions can be achieved by generating sequences in which the third position of one or more selected (or all) codons is substituted with mixed bases and/or deoxyinosine residues (Batzer et al., *Nucleic Acid Res.* 19:5081 (1991); Ohtsuka et al., *J Biol. Chem.* 260:2605-2608 (1985); and Rossolini et al., *Mol. Cell. Probes* 8:91-98 (1994)).

A "construct" refers to any recombinant polynucleotide molecule (such as plasmid, cosmid, virus, autonomously replicating polynucleotide molecule, phage, or linear or circular single- or double-stranded DNA or RNA polynucleotide molecule), derived from any source, capable of genomic integration or autonomous replication, comprising a polynucleotide molecule where one or more polynucleotide molecules have been linked in a functionally operative manner (i.e., operably linked). The recombinant construct will typically comprise a polynucleotide of the present invention operably linked to transcription initiation regulatory sequences that will direct transcription of the polynucleotide in a host cell. Both heterologous and non-heterologous (i.e., endogenous) promoters can be used to direct expression of the nucleic acids of the present invention.

A "vector" refers to any recombinant polynucleotide construct that can be used for transformation purpose (i.e., the introduction of heterologous DNA into a host cell). One type of vector is a "plasmid", which refers to a double-stranded DNA loop into which additional DNA segments can be ligated. Another type of vector is a viral vector, in which additional DNA segments can be ligated into the viral genome. Certain vectors are capable of autonomous replication in a host cell into which they are introduced (e.g., bacterial vectors having a bacterial origin of replication and episomal mammalian vectors). After introduction into a host cell, other vectors (e.g., non-episomal mammalian vectors) are integrated into genome of the host cell and are, thus, replicated along with the host genome. In addition, certain vectors are capable of directing the expression of operably linked genes. Such vectors are referred to herein as "expression vectors".

The term "expression vector" as used herein refers to a nucleic acid molecule capable of replicating and expressing a target gene when transformed, transfected or transduced into a host cell. The expression vector comprises one or more phenotypic selectable markers and an origin of replication to ensure maintenance of the vector and to provide amplification in the host if needed.

As used herein, the term "IL-17A antagonist" or "IL-17A blocker" refers to an antibody or an antigen-binding protein thereof that inhibits the signal transduction activity of IL-17A induced by IL-17R, thereby reducing or neutralizing IL-17A activity. This can be shown in assays for human cells such as IL-17A dependent CXCL1 production assays for human cells. Such assays are described in more detail in the examples below.

Unless otherwise or explicitly specified in the context, "activation", "stimulation" and "treatment" for a cell or a receptor may have the same meaning. For example, the cell or the receptor is activated, stimulated, or treated with a ligand. "Ligands" include natural and synthetic ligands, such as cytokines, cytokine variants, analogs, mutant proteins, and binding compounds derived from antibodies. "Ligands" also include small molecules, such as peptidomimetics of cytokines and peptidomimetics of antibodies. "Activation" may refer to the activation of a cell regulated by internal mechanisms as well as external or environmental factors. "Response/reaction", e.g., a response of a cell, a tissue, an organ, or an organism, includes changes in biochemical or physiological behaviors (e.g., concentration, density, adhesion or migration, gene expression rate, or differentiation state within a biological compartment), where the changes are associated with an activation, a stimulation or a treatment, or are associated with an internal mechanism such as genetic programming.

As used herein, the term "treat", "treating" or "treatment" of any disease or disorder refers in one embodiment to ameliorating the disease or disorder (i.e., slowing or arresting or reducing the progression of the disease or at least one of its clinical symptoms). In another embodiment, "treat", "treating" or "treatment" refers to ameliorating or improving at least one physical parameter, including those physical parameters that may not be discernible by the patient. In another embodiment, "treat", "treating" or "treatment" refers to modulating the disease or disorder, physically (e.g., stabilization of discernible symptoms), physiologically (e.g., stabilization of physical parameters), or both. Unless explicitly described herein, methods for assessing treatment and/or prevention of a disease are generally known in the art. A "subject" includes any human or non-human animal. The term "non-human animal" includes all vertebrates, e.g., mammals and non-mammals, such as non-human primates, sheep, dog, cat, horse, cattle, chicken, amphibians, and reptiles. As used herein, the term "cyno" refers to a cynomolgus monkey.

"Therapeutically effective amount", "therapeutically effective dose," and "effective amount" as used herein refer to an amount of the IL-17A antibody or the antigen-binding fragment thereof disclosed herein that is effective for preventing or improving one or more symptoms of a disease or condition or the development of the disease or condition, when administered alone or in combination with other therapeutic agents to a cell, tissue or subject. The therapeutically effective dose also refers to an amount of the antibody or the antigen-binding fragment thereof sufficient to cause an improvement in symptoms, e.g., an amount for treating, curing, preventing or improving a related condition or promoting the treatment, cure, prevention or improvement of such condition. When an active ingredient is administered to an individual alone, a therapeutically effective dose refers to the amount of the ingredient. When a combination is administered, a therapeutically effective dose refers to the combined amount of active ingredients that produces a therapeutic effect, regardless of whether these active ingredients are administered in combination, sequentially or simultaneously. An effective amount of the therapeutic agent will lead to an increase in a diagnostic index or parameter by at least 10%, generally at least 20%; preferably at least about 30%, more preferably at least 40%, most preferably at least 50%.

Production of Antibodies

Any suitable method for producing antibodies may be employed to produce the antibody disclosed herein. Any suitable form of human IL-17A may be used as an immunogen (antigen) for the production of antibodies. By way of example and not limitation, any human IL-17A isotype or a fragment thereof may be used as an immunogen. Examples include, but are not limited to the natural mature human IL-17A (having an amino acid sequence set forth in SEQ ID NO: 66) as described herein.

In a preferred embodiment, the hybridoma cells producing murine monoclonal anti-human IL-17A antibodies can be produced by methods well known in the art. These methods include, but are not limited to, hybridoma techniques originally developed by Kohler et al., (1975) (*Nature* 256:495-497). Preferably, mouse splenocytes are isolated and fused to a mouse myeloma cell line using PEG or by electrofusion according to standard schemes. The resulting hybridomas producing antigen-specific antibodies can then be screened. For example, in the case of 50% PEG, a single cell suspension of splenic lymphocytes derived from an immunized mouse can be fused to 1/6 number of mouse myeloma cells SP20 (ATCC). The cells can be seeded in a flat-bottomed microtiter plate at about $2 \times 10^5$ cells/mL, followed by 2 weeks of incubation in complete medium containing 20% fetal bovine serum and selection medium containing 1×HAT (Sigma; HAT added 24 h after fusion). After 2 weeks, the cells can be cultured in medium with HAT replaced with HT. Wells can then be screened by ELISA for anti-human IL-17A monoclonal IgG antibodies. In general, after 10-14 days of the large-scale growth of hybridomas, the medium can be observed. The hybridomas secreting antibodies can be seeded and screened again. If the resulting hybridomas remain positive for human IgG, the anti-human IL-17A monoclonal antibody hybridomas can be subcloned at least twice by limiting dilution. The stable subclones can then be cultured in vitro to produce small amounts of antibodies in tissue medium for characterization.

In a preferred embodiment, the monoclonal hybridoma cells obtained in the present invention are 1F8, 2F5, and 2B2 that secrete antibodies binding to IL-17A with high specificity, blocking the binding of IL-17A to IL-17RA, and inhibiting IL-17A-mediated bioactivity, such as inhibiting the secretion of CXCL1.

In a preferred embodiment, the DNA sequences of the immunoglobulin variable regions of candidate hybridoma cells 1F8, 2F5, and 2B2 are determined using degenerate primer-based PCR in the present invention. The hybridoma cell 1F8 produces two antibody light chain genes and one antibody heavy chain gene, and 2F5 produces two antibody heavy chain genes and one antibody light chain gene. Therefore, the antibodies secreted by 1F8 and 2F5 may each include two mixed intact antibodies. Herein, the antibodies secreted by 1F8 are coded as 1F8-1 and 1F8-2, and the antibodies secreted by 2F5 are coded as 2F5-1 and 2F5-2.

TABLE 1

Amino acid sequences of variable regions of hybridoma antibodies

| Hybridoma | Variable region | Amino acid sequence |
|---|---|---|
| 1F8-1 | VH | SEQ ID NO: 25 |
|  | VL1 | SEQ ID NO: 29 |
| 1F8-2 | VH | SEQ ID NO: 25 |
|  | VL2 | SEQ ID NO: 30 |
| 2B2 | VH | SEQ ID NO: 26 |
|  | VL | SEQ ID NO: 31 |
| 2F5-1 | VH1 | SEQ ID NO: 27 |
|  | VL | SEQ ID NO: 32 |
| 2F5-2 | VH2 | SEQ ID NO: 28 |
|  | VL | SEQ ID NO: 32 |

Antibodies derived from rodents (e.g., mouse) may induce unwanted immunogenicity of the antibodies when used as therapeutic agents in vivo. Repeated use of these antibodies induces an immune response in the human body to therapeutic antibodies. Such immune responses result in at least a loss of therapeutic efficacy and, at most, a potentially lethal allergic reaction. One method for reducing the immunogenicity of rodent antibodies includes producing chimeric antibodies, in which the mouse variable region is fused to the human constant region (Liu et al., (1987) *Proc. Natl. Acad. Sci. USA* 84:3439-43). However, the preservation of intact rodent variable region in chimeric antibodies can still induce deleterious immunogenicity in patients. Grafting of the complementarity determining region (CDR) loops of the rodent variable domain onto the human framework (i.e., humanization) has been used to further minimize rodent sequences (Jones et al., (1986) *Nature* 321:522; Verhoeyen et al., (1988) *Science* 239:1534).

In some embodiments, the chimeric or humanized antibodies disclosed herein can be prepared based on the sequences of the prepared murine monoclonal hybridoma antibodies. DNA encoding the immunoglobulin heavy and light chains can be obtained from a murine hybridoma of interest and engineered to comprise non-murine (e.g., human) immunoglobulin sequences using standard molecular biology techniques.

In some embodiments, for the chimeric antibodies disclosed herein, the chimeric heavy chain and the chimeric light chain can be obtained by operably linking the immunoglobulin heavy chain and light chain variable regions of hybridoma origin to human IgG constant regions respectively using methods known in the art (see, e.g., U.S. Pat. No. 4,816,567 to Cabilly et al.). The human IgG can be selected from any subtype, such as IgG1, IgG2, IgG3, IgG4, preferably IgG4.

In a specific embodiment, the chimeric antibodies disclosed herein can be obtained by "mixing and matching" a chimeric light chain expression plasmid with a chimeric heavy chain expression plasmid to transfect expression cells. The binding of such "mixed and matched" antibodies to IL-17A can be assayed using the above binding assay and other conventional binding assays (e.g., ELISA). The preferred ch1, ch2, ch4, ch7 and ch16 have optimal binding and blocking activity, and their amino acid sequences of variable region are shown in Table 2.

TABLE 2

Amino acid sequences of variable regions of chimeric antibodies

| Chimeric antibody | Heavy chain variable region (VH) | Light chain variable region (VL) |
|---|---|---|
| ch1 | SEQ ID NO: 25 | SEQ ID NO: 29 |
| ch2 | SEQ ID NO: 25 | SEQ ID NO: 30 |
| ch4 | SEQ ID NO: 25 | SEQ ID NO: 32 |
| ch7 | SEQ ID NO: 26 | SEQ ID NO: 31 |
| ch16 | SEQ ID NO: 28 | SEQ ID NO: 32 |

The precise amino acid sequence boundaries of the variable region CDRs in the antibodies disclosed herein may be determined using any of well-known schemes, including the Kabat scheme described by Kabat et al., (1991), *Sequences of Proteins of Immunological Interest*, 5th edition, Public Health Service, National Institutes of Health, Bethesda, MD ("Kabat" numbering scheme) and the IMGT scheme described by Lefranc M.-P. et al., (1999 *Nucleic Acids Research*, 27:209-212). In some embodiments, the specific CDR definition schemes and amino acid sequences of the variable regions of preferred murine antibodies disclosed herein are shown in Table 3.

In some embodiments, for the humanized antibodies disclosed herein, murine CDR regions can be inserted into human germline framework regions using methods known in the art. See U.S. Pat. No. 5,225,539 to Winter et al. and U.S. Pat. Nos. 5,530,101; 5,585,089; 5,693,762 and 6,180,370 to Queen et al. Briefly, human germline IgG genes homologous to the cDNA sequence of the murine antibody variable regions were retrieved in the human immunoglobulin gene database of the NCBI (ncbi.nlm.nih.gov/igblast/) by the inventor, and in principle, humanization is achieved by grafting of the selected CDRs. However, CDR loop exchange still fails to uniformly produce an antibody with the same binding properties as the initial antibody. In humanized antibodies, changes in framework residues (FRs) (residues involved in CDR loop support) are often required to maintain the antigen-binding affinity. Kabat et al., (1991) *J. Immunol.* 147:1709. Briefly, the humanization comprises the following steps: A. the gene sequences of the candidate antibodies are compared with the human germline antibody gene sequence to select sequences with high homology; B, by HLA-DR affinity analysis, a human germline framework sequence with low affinity is selected; and C, the framework amino acid sequences of the variable regions and their periphery are analyzed by computer simulation and molecular docking, and the spatial and stereo arrangement is verified. The key amino acid individuals that interact with IL-17A and maintain the spatial framework in the gene sequence of the candidate antibodies are analyzed by calculating electrostatic force, Van der Waals' force, hydrophilicity and hydrophobicity, and entropy value, and grafted to the selected human germline gene framework. The amino acid positions of the framework regions that must be retained are mapped. After that, the humanized antibodies are synthesized.

In some embodiments, preferred humanized antibodies obtained in the present invention are hu31, hu43, hu44, hu59, hu60 and hu250.

Variable regions of humanized antibodies hu31, hu43, hu44, hu59, hu60 and hu250 and their corresponding CDR amino acid sequences are shown in Table 4.

TABLE 3

| Variable region CDR definitions of murine antibodies | | | | | | |
|---|---|---|---|---|---|---|
| CDR definition scheme | IMGT scheme | | KABAT scheme | | | IMGT scheme |
| Antibody origin | 1F8-1 | 1F8-2 | 2B2 | 2F5-1 | | 2F5-2 |
| HCDR1 | SEQ ID NO: 1 | SEQ ID NO: 1 | SEQ ID NO: 4 | SEQ ID NO: 7 | SEQ ID NO: 10 | SEQ ID NO: 60 |
| HCDR2 | SEQ ID NO: 2 | SEQ ID NO: 2 | SEQ ID NO: 5 | SEQ ID NO: 8 | SEQ ID NO: 11 | SEQ ID NO: 61 |
| HCDR3 | SEQ ID NO: 3 | SEQ ID NO: 3 | SEQ ID NO: 6 | SEQ ID NO: 9 | SEQ ID NO: 12 | SEQ ID NO: 62 |
| LCDR1 | SEQ ID NO: 13 | SEQ ID NO: 16 | SEQ ID NO: 19 | SEQ ID NO: 22 | SEQ ID NO: 22 | SEQ ID NO: 63 |
| LCDR2 | SEQ ID NO: 14 | SEQ ID NO: 17 | SEQ ID NO: 20 | SEQ ID NO: 23 | SEQ ID NO: 23 | SEQ ID NO: 64 |
| LCDR3 | SEQ ID NO: 15 | SEQ ID NO: 18 | SEQ ID NO: 21 | SEQ ID NO: 24 | SEQ ID NO: 24 | SEQ ID NO: 65 |

TABLE 4

Variable regions and CDR sequences of humanized antibodies

| Antibody | hu31 | hu43 | hu44 | hu59 | hu60 | hu250 |
|---|---|---|---|---|---|---|
| VH | SEQ ID NO: 33 | SEQ ID NO: 35 | SEQ ID NO: 35 | SEQ ID NO: 37 | SEQ ID NO: 37 | SEQ ID NO: 40 |
| VL | SEQ ID NO: 34 | SEQ ID NO: 34 | SEQ ID NO: 36 | SEQ ID NO: 38 | SEQ ID NO: 39 | SEQ ID NO: 41 |
| HCDR1 | SEQ ID NO: 1 | SEQ ID NO: 1 | SEQ ID NO: 1 | SEQ ID NO: 10 | SEQ ID NO: 10 | SEQ ID NO: 60 |
| HCDR2 | SEQ ID NO: 2 | SEQ ID NO: 2 | SEQ ID NO: 2 | SEQ ID NO: 11 | SEQ ID NO: 11 | SEQ ID NO: 61 |
| HCDR3 | SEQ ID NO: 3 | SEQ ID NO: 3 | SEQ ID NO: 3 | SEQ ID NO: 12 | SEQ ID NO: 12 | SEQ ID NO: 62 |
| LCDR1 | SEQ ID NO: 13 | SEQ ID NO: 13 | SEQ ID NO: 13 | SEQ ID NO: 22 | SEQ ID NO: 22 | SEQ ID NO: 63 |
| LCDR2 | SEQ ID NO: 14 | SEQ ID NO: 14 | SEQ ID NO: 14 | SEQ ID NO: 23 | SEQ ID NO: 23 | SEQ ID NO: 64 |
| LCDR3 | SEQ ID NO: 15 | SEQ ID NO: 15 | SEQ ID NO: 15 | SEQ ID NO: 24 | SEQ ID NO: 24 | SEQ ID NO: 65 |

Amino acid and nucleotide sequences of light/heavy chain of humanized antibodies hu31, hu43, hu44, hu59, hu60 and hu250 are shown in Table 5.

TABLE 5

Amino acid/nucleotide sequences of humanized antibodies

| Humanized antibody | Heavy chain (HC) | | Light chain (LC) | |
|---|---|---|---|---|
| | Amino acid sequence | Nucleotide sequence | Amino acid sequence | Nucleotide sequence |
| hu31 | SEQ ID NO: 42 | SEQ ID NO: 51 | SEQ ID NO: 43 | SEQ ID NO: 52 |
| hu43 | SEQ ID NO: 44 | SEQ ID NO: 53 | SEQ ID NO: 43 | SEQ ID NO: 52 |
| hu44 | SEQ ID NO: 44 | SEQ ID NO: 53 | SEQ ID NO: 45 | SEQ ID NO: 54 |
| hu59 | SEQ ID NO: 46 | SEQ ID NO: 55 | SEQ ID NO: 47 | SEQ ID NO: 56 |
| hu60 | SEQ ID NO: 46 | SEQ ID NO: 55 | SEQ ID NO: 48 | SEQ ID NO: 57 |
| hu250 | SEQ ID NO: 49 | SEQ ID NO: 58 | SEQ ID NO: 50 | SEQ ID NO: 59 |

The other antibodies disclosed herein include those having an amino acid sequence that has been mutated by amino acid deletion, insertion or substitution, but still has at least 70%, 75%, 80%, 85%, 90%, 91%, 92%, 93%, 94%, 95%, 96%, 98%, 99% or 100% identity to the above antibodies (particularly in the CDR regions set forth in the above sequences). In some embodiments, the antibody disclosed herein is a mutant of any of hu31, hu43, hu44, hu59, hu60, and hu250, wherein the mutant comprises a mutant amino acid sequence in which no more than 1, 2, 3, 4 or 5 amino acids have been mutated by amino acid deletion, insertion or substitution in a CDR region when compared to the CDR regions set forth in the above sequences.

The other nucleic acids encoding the antibody disclosed herein include those that have been mutated by nucleotide deletion, insertion or substitution, but still have at least 60%, 70%, 80%, 90%, 95% or 100% identity to the corresponding CDR coding regions set forth in the above sequences.

Expression of Antibodies

In some embodiments, the present invention relates to one or more expression vectors or a host cell comprising the expression vectors and a method for producing the antibody or the antigen-binding fragment thereof disclosed herein, wherein the method comprises culturing the host cell, and purifying and isolating the antibody or the antigen-binding fragment thereof. The antibodies disclosed herein can be produced in host expression cells using, for example, a combination of recombinant DNA technique and gene transfection method well known in the art (e.g., Morrison, S. 1985, *Science* 229:1202). For example, for the expression of an antibody or an antibody fragment thereof, DNA encoding partial or full-length light and heavy chains can be obtained using standard molecular biology or biochemical techniques (e.g., DNA chemical synthesis, PCR amplification, or cDNA cloning using hybridomas expressing an antibody of interest), and the DNA can be inserted into an expression vector such that the genes are operably linked to transcriptional and translational control sequences. In this specification, the term "operably linked" means that the antibody genes are linked into a vector such that the transcriptional and translational control sequences in the vector perform their intended functions of regulating the transcription and translation of the antibody genes. The expression vector and expression control sequences that can be compatible with the expression host cell used are selected. The antibody light chain gene and the antibody heavy chain gene can be inserted into different vectors, or more typically, both genes are inserted into the same expression vector. An antibody gene is inserted into an expression vector by standard methods (e.g., ligation of the antibody gene fragment and complementary restriction sites on the vector, or blunt end ligation if no restriction site is present). Full-length antibody genes of any antibody isotype can be obtained by inserting the light and heavy chain variable regions of the antibody described herein into an expression vector that already encodes the heavy and light chain constant regions of the desired isotype to enable the operable linking of the VH segments to the CH segments in the vector and the operable linking of the VL segments to the CL segments in the vector. Additionally or alternatively, the recombinant expression vector may encode a signal peptide (also referred to as a leader sequence) that facilitates the secretion of an antibody chain from a host cell. The antibody chain gene can be cloned into a vector such that the signal peptide is linked to the amino terminus of the antibody chain gene in the same reading frame. The signal peptide may be an immunoglobulin signal peptide or a heterologous signal peptide (i.e., a signal peptide from a non-immunoglobulin protein).

Mammalian host cells for the expression of the recombinant antibodies disclosed herein include a number of immortalized cell lines available from American Type Culture Collection (ATCC). These include, in particular, Chinese hamster ovary (CHO) cells, NS0, SP2/0 cells, HeLa cells, baby hamster kidney (BHK) cells, monkey kidney cells (COS), human hepatocellular carcinoma cells, A549 cells, 293T cells, and many other cell lines. Mammalian host cells include human, mouse, rat, dog, monkey, pig, goat, cow, horse, and hamster cells. Particularly preferred cell lines are selected by determining which cell line has high expression level.

When a recombinant expression vector encoding a heavy chain or an antigen-binding fragment thereof or a fragment thereof, a light chain and/or an antigen-binding fragment thereof is introduced into a mammalian host cell, an antibody is produced by culturing the host cell for a sufficient period of time to allow the antibody to be expressed in the host cell, or more preferably, by secreting the antibody into a medium in which the host cell is grown. The antibody can be isolated from the medium using standard protein purification methods. It is likely that antibodies expressed by different cell lines or in transgenic animals have different glycosylations from each other. However, all antibodies encoded by the nucleic acid molecules provided herein or comprising the amino acid sequences provided herein are integral parts of the present invention, regardless of the glycosylation of the antibody. Likewise, in certain embodiments, nonfucosylated antibodies are advantageous because they generally have more potent efficacy in vitro and in vivo than their fucosylated counterparts, and are unlikely to be immunogenic because their glycan structures are normal components of natural human serum IgG.

Medical Use

The antibody or the antigen-binding fragment thereof disclosed herein has in vitro and in vivo diagnostic and therapeutic uses. Preferably, the humanized antibody hu31, hu43, hu44, hu59, hu60 or hu250 is useful for treating IL-17A-related diseases or disorders.

In one aspect, the isolated antibody or the antigen-binding fragment thereof disclosed herein is capable of resisting the onset of imiquimod-induced psoriasis in the mouse model, and reducing the clinical score of the psoriasis onset in mice and the degree of ear swelling of mice, when assessed for activity in vivo.

In a specific embodiment, in the imiquimod-induced psoriasis model, the humanized antibodies hu31 and hu44 can significantly resist the onset of mice, and reduce the clinical score of the psoriasis onset in mice and the degree of ear swelling of mice.

In one aspect, the isolated antibody or the antigen-binding fragment thereof disclosed herein is capable of inhibiting knee joint swelling in antigen-induced arthritis models, such as cynomolgus monkey AIA-model, when assessed in vivo.

In a specific embodiment, in the cynomolgus monkey AIA-model, the humanized antibody hu31 significantly inhibits the increasing trend in clinical score of arthritis in cynomolgus monkeys.

In one aspect of the present invention, provided is a method for treating pathological diseases mediated by IL-17A, comprising administering an effective amount of the isolated antibody or the antigen-binding fragment thereof according to the present invention, specifically hu31, hu43, hu44, hu59, hu60, or hu250 antibody, so as to alleviate the disorder.

In one embodiment, the isolated antibody or the protein comprising an antigen-binding fragment thereof disclosed herein is conjugated to another active moiety.

In one embodiment, the isolated antibody or the protein comprising the antigen-binding fragment thereof disclosed herein may be a monoclonal antibody or an antigen-binding fragment thereof, preferably a chimeric antibody, a humanized antibody or a human antibody or a portion thereof.

In aspects of the present invention, provided is a pharmaceutical composition comprising the antibody or the protein comprising the antigen-binding fragment thereof according to the embodiments described herein, in combination with one or more pharmaceutically acceptable excipients, diluents or carriers.

In embodiments, the pharmaceutical composition comprises one or more additional active ingredients.

In one specific embodiment, the pharmaceutical composition is a lyophilized powder. In another specific embodiment, the pharmaceutical composition is a stable liquid formulation comprising a therapeutically acceptable amount of the antibody or the molecule disclosed herein.

In particular, the present invention provides a method for treating IL-17A-related disorders and/or autoimmune and inflammatory disorders. In certain embodiments, the method comprises administering to a subject in need thereof the isolated antibody or the antigen-binding fragment thereof according to the present invention.

The present invention also provides a method for attenuating or inhibiting a signal transduction response induced by IL-17A or IL-17AF in a target cell or tissue by contacting a cell with a composition comprising a therapeutically effective dose of the antibody disclosed herein. In the present invention, the term "IL-17A-mediated disease" or "IL-17A-related disorder" includes all diseases and conditions in which IL-17A or IL-17AF play a role (whether directly or indirectly), including the cause, development, progression, persistence or pathology of the disease or condition. Thus, these terms include conditions associated with or characterized by abnormal IL-17A or IL-17AF level and/or diseases or conditions that can be treated by attenuating or inhibiting IL-17A/AF-induced activity (e.g., CXCL1) in a target cell or tissue. Such diseases or conditions include inflammatory conditions and autoimmune diseases such as arthritis, rheumatoid arthritis, ankylosing spondylitis, multiple sclerosis or psoriasis. Such diseases also include allergies and allergic conditions, hypersensitivity reactions, chronic obstructive pulmonary disease, cystic fibrosis, and organ or tissue transplant rejection.

As used herein, "inhibit" or "treat" or "treatment" includes delay in the development of symptoms associated with a disorder and/or reduction in the severity of symptoms of such disorders. The term also includes ameliorating existing uncontrolled or harmful symptoms, preventing other symptoms, and ameliorating or preventing the underlying causes of such symptoms. Thus, the term indicates that a beneficial result has been provided to a vertebrate subject suffering from or likely to suffer from a disorder, disease or condition.

The terms "therapeutically effective amount", "therapeutically effective dose," and "effective amount" as used herein refer to an amount of an IL-17 conjugate disclosed herein that is effective for preventing or improving one or more symptoms of a disease or condition or the development of the disease or condition, when administered alone or in combination with other therapeutic agents to a cell, tissue or subject. The therapeutically effective dose also refers to an amount of the conjugate sufficient to cause an improvement in symptoms, e.g., an amount for treating, curing, preventing or improving a related condition or promoting the treatment, cure, prevention or improvement of such condition. When an active ingredient is administered to an individual alone, a therapeutically effective dose refers to the amount of the ingredient. When a combination is administered, a therapeutically effective dose refers to the combined amount of active ingredients that produces a therapeutic effect, regardless of whether these active ingredients are administered in combination, sequentially or simultaneously. An effective amount of the therapeutic agent will result in an increase in a diagnostic index or parameter by at least 10%, generally at least 20%; preferably at least about 30%, more preferably at least 40%, most preferably at least 50%.

Rheumatoid Arthritis (RA) RA is a progressive systemic disease characterized by inflammation of synovial joints, affecting approximately 0.5% of the global population. See Emery, (2006) BMJ 332:152-155. Inflammation of joints may lead to deformity, pain, stiffness and swelling, and ultimately to irreversible degeneration of joints. Affected joints include knee, elbow, neck and extremity joints. Conventional treatments include symptomatic treatment with NSAIDs, followed by treatment with disease-modifying anti-rheumatic drugs (DMRDs), such as gold, penicillamine, sulfasalazine, and methotrexate. Recent advances include treatment with TNF-α inhibitors, including monoclonal antibodies such as infliximab, adalimumab, and golimumab, and receptor fusion proteins such as etanercept. Treatment with such TNF-alpha inhibitors significantly reduces structural damage due to the disease.

The anti-IL-17A antibodies disclosed herein may be used to treat RA in a subject in need for such treatment. The anti-IL-17A antibodies disclosed herein may also be combined with other treatments for RA, such as methotrexate, azathioprine, cyclophosphamide, ethyl mycophenolate, NSAIDs or TNF-α inhibitors.

Psoriasis

Skin is an important barrier between the internal and external environment, preventing contact with potentially harmful antigens. In the case of antigen/pathogen invasion, T cells, polymorphonuclear cells, macrophages and the like at the skin contact site locally infiltrate and an inflammatory response is initiated to eliminate the antigen. (see, e.g., Williams and Kupper, (1996) Life Sci., 58:1485-1507). Generally, this inflammatory response triggered by the pathogen is under strict control and is terminated when the pathogen is eliminated. In some cases, such inflammatory response occurs without external irritation and without proper control, resulting in skin inflammation. The present invention provides a method for treating and diagnosing such skin inflammation. Skin inflammation (a consequence of the aforementioned cellular infiltration and cytokines secreted by the cells) includes several inflammatory conditions such as cicatricial pemphigoid, scleroderma, hidradenitis suppurativa, toxic epidermal necrolysis, acne, osteitis, graft versus host disease (GVHD), pyoderma gangrenosum and Behcet's syndrome (see, e.g., Williams and Griffiths, (2002) Clin. Exp. Dermatol., 27:585-590). The most common skin inflammation is psoriasis. Psoriasis is characterized by T cell-mediated keratinocyte hyperproliferation with inflammatory infiltration. The disease has some shared manifestations, including chronic plaque lesions, rash, and pustular lesions (see, e.g., Gudjonsson et al., (2004) Clin. Exp. Immunol. 135:1-8). About 10% of patients with psoriasis may develop arthritis. The disease has a strong and complicated genetic predisposition with a 60% identity in monozygotic twins.

Typical psoriatic lesions are red plaques with clear edge covered by thick silvery scales. Inflammation and hyperproliferation of psoriatic tissue are associated with different histological, antigenic and cytokine profiles compared to normal skin. Cytokines associated with psoriasis are: TNF-α, IL-19, IL-18, IL-15, IL-12, IL-7, IFN-γ, IL-17A and IL-23 (see Gudjonsson et al., supra).

The anti-IL-17A antibodies disclosed herein, alone or in combination with other agents, may also be used to prevent, treat, diagnose and predict psoriasis onset.

To prepare a pharmaceutical or sterile composition of the IL-17A antibody disclosed herein, the antibody is mixed with a pharmaceutically acceptable carrier or excipient. See, e.g., *Remington's Pharmaceutical Sciences* and U.S. Pharmacopeia: National Formulary, Mack Publishing Company, Easton, PA (1984).

The following dosage forms of therapeutic and diagnostic agents may be prepared by mixing the antibody with an acceptable carrier, excipient or stabilizer: a lyophilized powder, a paste, an aqueous solution or a suspension. In one embodiment, the IL-17A antibody disclosed herein is diluted to an appropriate concentration by a sodium acetate solution (pH 5-6), and added with NaCl or sucrose to adjust osmolality. Other substances (e.g., polysorbate 20 or polysorbate 80) may be added to improve stability.

The dosage regimen depends on several factors including serum or tissue turnover of the therapeutic antibody, severity of symptoms, immunogenicity of the therapeutic antibody, and accessibility of the target cells in the biological matrix. Preferably, the dosage regimen delivers a sufficient amount of therapeutic antibody to achieve an improvement in the target disease state while minimizing adverse side effects. Thus, the amount of biologics delivered depends in part on the particular therapeutic antibody and the severity of the condition to be treated. Guidance regarding selections of appropriate dosages for therapeutic antibody is available. Appropriate dosages can be determined by the clinician, for example, using parameters or factors known or suspected in the art affecting treatment. In general, the dosage starts at an amount slightly less than the optimal dose and will be increased in small increments thereafter until the desired or optimal effect is achieved relative to any negative side effects. Important diagnostic methods include, for example, diagnostic methods based on inflammatory symptoms or levels of inflammatory cytokines produced. Preferably, biologics derived from the same species as the animal for the targeted therapy are used, thereby minimizing inflammatory, autoimmune or proliferative responses to the agent. For example, in the case of human subjects, chimeric, humanized and fully human antibodies are preferred. The present invention includes any combinations of the specific embodiments described. Further embodiments of the present invention and the full scope of applicability will become apparent from the detailed description provided below. However, it should be understood that the detailed description and the specific examples, while indicating preferred embodiments of the present invention, are provided by way of illustration only, as various changes and modifications within the spirit and scope of the present invention will become apparent to those skilled in the art from the detailed description. All publications, patents and patent applications cited herein, including the citations, are hereby incorporated by reference in their entirety for all purposes.

EXAMPLES

Example 1. Recombinant human IL-17A-mFc protein

Plasmid HG12047-G containing the cDNA sequence encoding full-length human IL-17A (NCBI Accession No. NP_002181.1) was purchased from Sino Biological, Inc., and a mature fragment of human IL-17A (amino acids 24-155 of NCBI Accession No. NP_002181.1, amino acid sequence of SEQ ID NO: 66, nucleotide sequence of SEQ ID NO: 67) was amplified by conventional PCR techniques. The amplified fragment was digested by BSPQI, and was cloned into a eukaryotic expression plasmid system (MXT1-Fc, containing the Fc domain of murine IgG heavy chain) constructed in-house, thereby generating an expression plasmid for recombinant fusion protein IL-17A-mFc. Verified plasmid was transfected into the expression cell 293F by conventional techniques, and the recombinant human IL-17A-mFc protein was acquired after expression and purification. FIG. 1 shows the SDS-PAGE electropherogram of the recombinant human IL-17A-mFc protein.

Example 2. Construction of Stable 293F Cell Lines Expressing Human IL-17RA

Plasmid HG10895-G containing the cDNA sequence encoding full-length human IL-17RA was purchased from Sino Biological, Inc., and the DNA sequence encoding full-length human IL-17RA was amplified by conventional PCR (SEQ ID NO: 69). The amplified fragments were cloned into a eukaryotic expression plasmid system (HXP) constructed in-house containing puromycin screening system by conventional cloning techniques. Verified recombinant expression plasmid for IL-17RA was transfected into 293F cells (ATCC). 24 h after transfection, cells were selected by puromycin (2 μg/mL) until stable IL-17RA 293F cells were generated. Individual clones were isolated by conventional methods, e.g., by limiting dilution cloning, and transferred into 96-well plates at 0.8 cells per well. 15 days later, IL-17RA-293F monoclones were selected and passaged to give stable IL-17RA 293F cell lines. All clones were screened by FACS or the like, and clones with top expression level were selected by FACS binding assay for hybridoma monoclonal antibodies or for use in functional assays.

Figure 2:
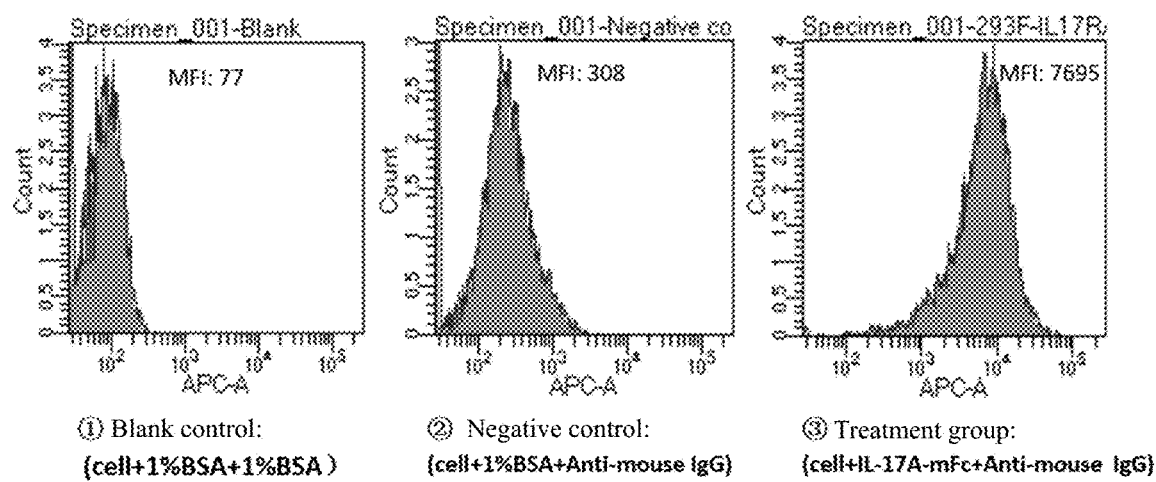
FIG. 2 shows the binding of human IL-17A-mFc to IL-17RA on 293F cells assayed by FACS (MFI represents mean fluorescence intensity; treatment group vs. control group: 7695 vs. 308).

Example 3. Binding of Recombinant IL-17A-mFc Protein to Stable IL-17RA 293F Cell Lines The binding specificity of the recombinant IL-17A-mFc protein to IL-17RA on 293F cells was determined by FACS. Briefly, cells (stable IL-17RA 293F cell lines) were prepared into cell suspensions at $1\times10^6$/mL, and added to 96-well plates at 20 μL/well, with an actual cell number of $2\times10^4$/well. The recombinant IL-17A-mFc protein (3 μg/mL, 20 μL/well; treatment group) or 1% BSA (20 μL/well; negative control group) was mixed with the cell suspension, and after an incubation at 37° C. for 30 minutes, the cells were washed with FACS buffer 3 times. Anti-mouse IgG (1:200) was added and the cells were incubated at room temperature for 30 minutes. The cells were washed 3 times with FACS buffer and detected by a flow cytometer to compare the mean fluorescence intensity (MFI) of the groups. As shown in FIG. 2, the recombinant IL-17A-mFc protein can specifically bind to IL-17RA on 293F cells.

Example 4. Preparation and Screening of Hybridoma Antibodies

Hybridoma antibodies were produced using standard molecular biological techniques. Briefly, native human IL-17A protein purchased from HumanZyme as an antigen was mixed with an equal amount of an immunoadjuvant. 5 female FVB mice aged 6 weeks were immunized. One booster immunization was performed weekly after the primary immunization, totaling seven immunizations. After the last booster immunization, mice with high anti-IL-17A antibody titers in serum were selected for cell fusion. Spleen cells were isolated and fused with the murine myeloma SP2/0 cells (ATCC) by standard hybridoma techniques. The fused cells were resuspended in complete medium RPMI-1640 containing HAT and plated in wells with a feeder layer of peritoneal cells.

Monoclonal hybridoma secretory supernatants were identified based on initially desired antibody/antigen binding characteristics (such as binding affinity for IL-17A, ability to block the binding of IL-17A to its receptor, cross-reactivity, and ability to block IL-17A-mediated biological effects in vitro). Antibodies in supernatant from hybridomas 1F8, 2B2, 2F5, 2F2, 2H1 and 2H5 were used for further characterization.

Example 5. Effects of Hybridoma Antibodies in Blocking IL-17A Bioactivity In Vivo A large number of researches show that IL-17A promotes the expression and release of cytokine CXCL1 in vivo. Thus the expression change of CXCL1 in mouse serum can be quantitatively detected through ELISA, so as to determine the influence of a hybridoma antibody on IL-17A-mediated bioactivity in mice. Briefly, 40 female Balb/c mice aged 10 weeks were selected and divided into 8 groups of 5 mice each. 4 days before administration, serum was collected and CXCL1 expression was measured as the baseline. On the day of administration, candidate hybridoma antibodies, saline (control) or reference antibody mAb317 (commercially available anti-IL-17A antibody, from R&D) was administered intracardially at a dose of 1 mg/kg. 1 hour after administration, native human IL-17A (HumanZyme) was injected subcutaneously at a dose of 150 μg/kg; 2 hours after the administration of human IL-17A, serum was collected, and the blood CXCL1 concentration was measured and compared with the baseline. The fold change (mean±standard error (mean SEM)) in CXCL1 concentration before and after administration was calculated for each group. Comparative analysis between treatment groups and the control group is considered significantly different when P is <0.05 in a Student's t test, *P<0.05, P<0.01, *P<0.001.

Figure 3:
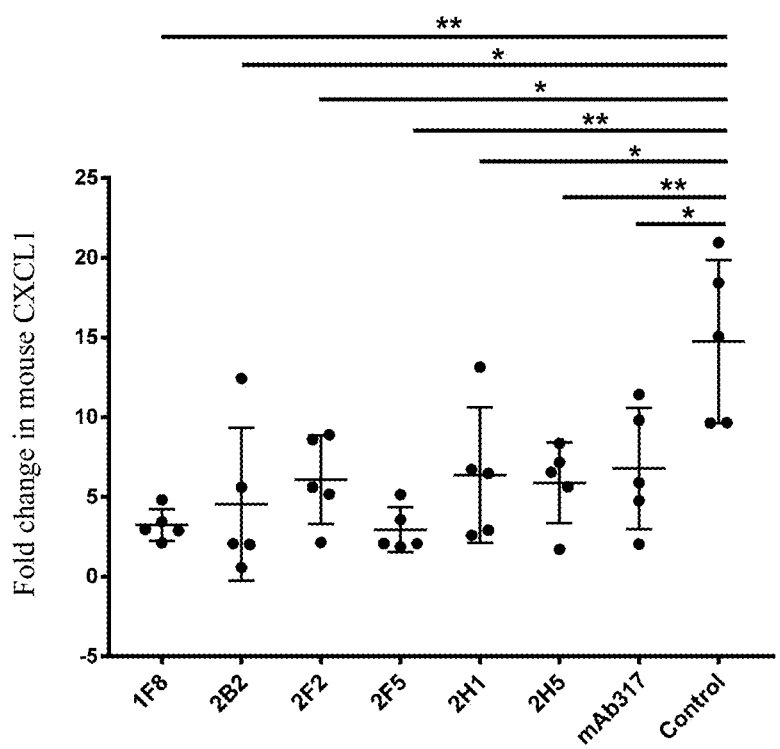
FIG. 3 shows the effect of hybridoma antibody on blocking IL-17A-mediated bioactivity in vivo assayed by ELISA. The hybridoma antibody significantly inhibits IL-17A from inducing the expression of CXCL1 in mice.

As shown in FIG. 3, the hybridoma antibodies obtained in Example 4 and the commercial antibody mAb317 both can significantly inhibited IL-17A from inducing CXCL1 expression in mice.

Example 6. Acquisition of Variable Region Sequences of Candidate Antibodies

The DNA sequences of the antibody variable regions expressed by hybridomas 1F8, 2B2 and 2F5 were determined using degenerate primer-based PCR. Briefly, hybridoma cell lines 1F8, 2B2 and 2F5 were expanded and harvested by centrifugation at 1000 rpm. Total RNA was extracted using Trizol. Using the total RNA as a template, a first-strand cDNA was synthesized. DNA sequences of corresponding variable regions were amplified by PCR using the first-strand cDNA as a subsequent template. The PCR primers used were based on an Ig-primer set. PCR products were collected, purified, sequenced and analyzed to give the variable region sequences of the heavy and light chains of the candidate hybridoma antibodies. The hybridoma cell 1F8 produced two antibody light chain variable region gene sequences and one antibody heavy chain variable region gene sequence, and 2F5 produced two antibody heavy chain variable region gene sequences and one antibody light chain variable region gene sequence. Therefore, the antibodies secreted by 1F8 and 2F5 might each include two intact antibodies, wherein the antibodies secreted by 1F8 were coded as 1F8-1 and 1F8-2, and the antibodies secreted by 2F5 were coded as 2F5-1 and 2F5-2.

The amino acid sequences of the heavy and light chain variable regions of the antibodies expressed by 1F8, 2F5, 2B2 are shown in Table 1 (see DETAILED DESCRIPTION).

Example 7. Construction of Recombinant Chimeric Antibody Expression Vectors

Human IgG4 heavy chain constant region Fc fragment and light chain kappa constant region were cloned from human blood cells (Beijing Blood Institute) and ligated with pCDNA3.1 plasmid for engineering. The heavy chain and light chain variable region sequence fragments were synthesized by GenScript. The heavy and light chains were cleaved by Bspq I, and then ligated to a correspondingly modified pCDNA3.1 plasmid. The expression plasmids of IgG4 chimeric heavy chain (ch-HC) or light chain (ch-LC) were verified by sequencing. The expression plasmids for the different chimeric heavy and light chains were paired to transfect expression cells, producing 16 chimeric antibodies numbered ch1 to ch16 (see Table 6). All subsequent experimental materials were given by the expression cells transfected with these plasmids.

TABLE 6

Chimeric antibody light/heavy chain source

| LC/HC | 1F8-ch-HC | 2B2-ch-HC | 2F5-ch-HC1 | 2F5-ch-HC2 |
|---|---|---|---|---|
| 1F8-ch-LC1 | ch1 | ch5 | ch9 | ch13 |
| 1F8-ch-LC2 | ch2 | ch6 | ch10 | ch14 |
| 2B2-ch-LC | ch3 | ch7 | ch11 | ch15 |
| 2F5-ch-LC | ch4 | ch8 | ch12 | ch16 |

Example 8. Binding Specificity of Chimeric Antibodies to Human IL-17A

The binding specificity of the chimeric antibodies to human IL-17A was determined by conventional ELISA. Namely, 0.5 µg/mL of human IL-17A-mFc was immobilized on a 96-well plate and incubated for 60-90 minutes at 37° C. The solution in wells was then discarded, and the wells were washed 3 times with washing buffer, and blocked for 60 minutes with PBS containing 2% BSA. The plate was washed 3 times with washing buffer, and added with diluted chimeric antibodies at different concentrations. The antibodies were incubated at 37° C. for 60 minutes. The plate was then washed 3 times with washing buffer, and added with 10000-fold diluted biotinylated anti-IgG4 antibody. The system was incubated at 37° C. for 1 hour, washed three times with washing buffer, added with HRP-Strep 10000-fold diluted with washing buffer, and incubated at room temperature for 1 hour. After 3 washes with washing buffer, 100 µL of TMB substrate was added for color development. The system was incubated at room temperature for 30 minutes, and the reaction was terminated with 100 µL of 2 M hydrochloric acid solution. The absorbance at 450 nm was measured by a plate reader.

Figure 4:
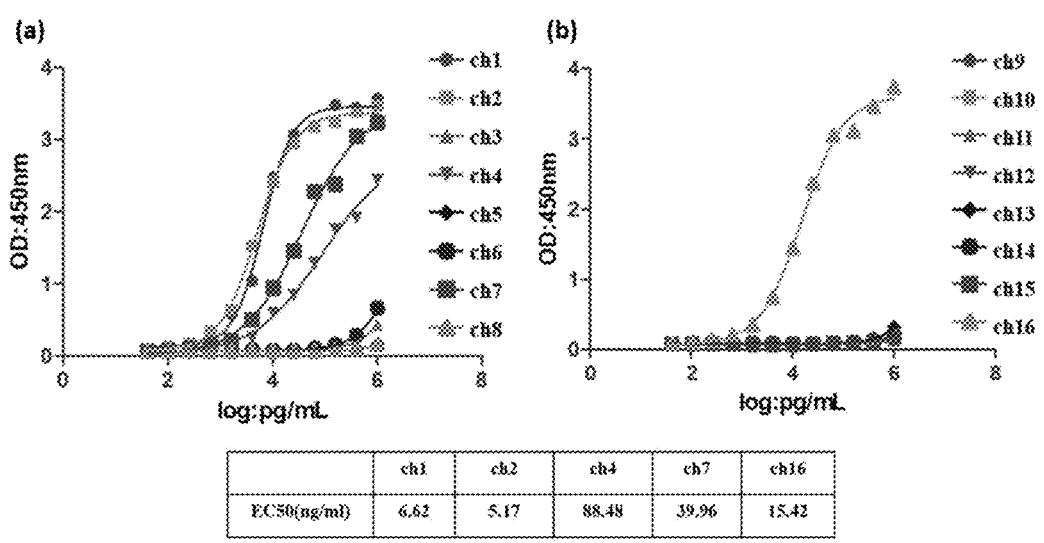
FIG. 4 shows the binding of chimeric antibodies to human IL-17A assayed by ELISA. The chimeric antibodies ch1, ch2, ch4, ch7 and ch16 bind to human IL-17A with higher specificity, with the $EC_{50}$ values being 6.62 ng/mL, 5.17 ng/mL, 88.48 ng/mL, 39.96 ng/mL and 15.42 ng/mL, respectively.

As shown in FIG. 4, chimeric antibodies ch1, ch2, ch4, ch7 and ch16 bind to human IL-17A with higher specificity, with the $EC_{50}$ of the chimeric antibodies being 6.62 ng/mL, 5.17 ng/mL, 88.48 ng/mL, 39.96 ng/mL and 15.42 ng/mL, respectively.

Example 9. Blocking of Binding of Human IL-17A to IL-17RA by Chimeric Antibodies The blocking of binding of IL-17A to IL-17RA on cells was detected by a competitive cell-based flow cytometry (FACS) assay. Briefly, chimeric antibody dilutions of different concentrations (3-fold diluted from 10 µg/mL) were mixed with the pre-biotinylated human IL-17A-mFC (3 µg/mL) obtained in Example 1, and incubated at room temperature for 30 minutes. The mixture was then co-incubated with a cell suspension (stable IL-17RA 293F cell lines obtained in Example 2, $1.5 \times 10^5$ cells/well) at 37° C. for 15 minutes. After 3 washes with PBS, 5 µg/mL of anti-mouse IgG was added and the system was incubated at room temperature for 30 minutes. After 3 washes with PBS, the chimeric antibodies were analyzed by flow cytometry for inhibiting the binding of IL-17A to IL-17RA on the surface of 293F cells.

Figure 5:
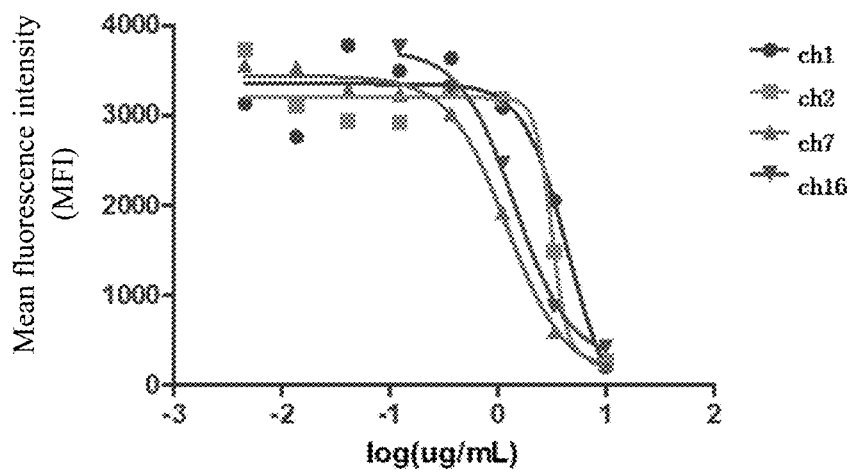
FIG. 5 shows the effect of chimeric antibodies on blocking the binding of human IL-17A to IL-17RA on 293F cells assayed by FACS. The chimeric antibodies ch1, ch2, ch7 and ch16 block the binding efficiently, with the $IC_{50}$ values being 4.46 µg/mL, 3.145 µg/mL, 1.220 µg/mL and 1.445 µg/mL, respectively.

As shown in FIG. 5, chimeric antibodies ch1, ch2, ch7 and ch16 can significantly inhibit the binding of human IL-17 to IL-17RA on the surface of 293F cells. Combining other experimental results, ch1 and ch16 were selected for further humanization.

Example 10. Humanization of Antibodies

For humanization of antibodies, human IgG genes homologous to the cDNA sequence of the murine antibody variable regions were retrieved in the human immunoglobulin gene database of the NCBI (ncbi.nlm.nih.gov/igblast/). The amino acid sequences of CDRs of the variable regions and their boundaries were then determined as per the Kabat numbering system or the IMGT numbering system. Human IGVH and IGVk with high homology to the variable regions of the murine antibody were selected as templates for humanization, and were humanized by CDR grafting. Briefly, the humanization comprises the following steps: A. the gene sequences of the candidate antibodies were compared with the human germline antibody gene sequence to select sequences with high homology; B. by HLA-DR affinity analysis, a human germline framework sequence with low affinity was selected; and C. the framework amino acid sequences of the variable regions and their periphery were analyzed by computer simulation and molecular docking, and the spatial and stereo arrangement was verified. The key amino acid individuals that interact with IL-17A and maintain the spatial framework in the gene sequence of the candidate antibodies were analyzed by calculating electrostatic force, Van der Waals' force, hydrophilicity and hydrophobicity, and entropy value, and grafted to the selected human germline gene framework. The amino acid positions of the framework regions that must be retained were mapped. After that, the humanized antibodies were synthesized.

The definition scheme of the variable region CDRs of murine antibodies and their amino acid sequences are shown in Table 3 of the DETAILED DESCRIPTION.

Based on the aforementioned results, chimeric antibodies ch1 and ch16 were selected for humanization. Following a primary screening of a series of antibody/antigen-binding properties (such as binding affinity for IL-17A, ability to block the binding of IL-17A to its receptor), humanized antibodies hu31, hu43, hu44, hu59, hu60 and hu250 were selected for subsequent validation.

Variable regions of humanized antibodies hu31, hu43, hu44, hu59, hu60 and hu250 and their CDR amino acid sequences are shown in Table 4 of the DETAILED DESCRIPTION.

Example 11. Binding Specificity of Humanized Antibodies to Human IL-17A

Figure 6:
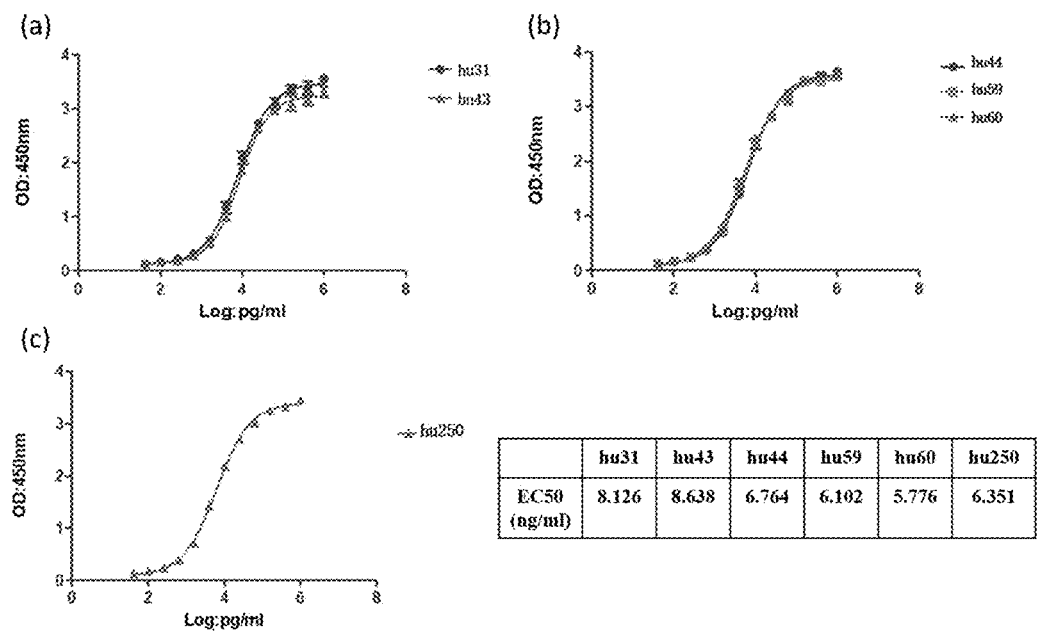
FIG. 6 shows the binding of humanized antibodies to human IL-17A assayed by ELISA. The antibodies hu31, hu43, hu44, hu59, hu60 and hu250 bind to human IL-17A with higher specificity, with the $EC_{50}$ values being 8.13 ng/mL, 8.64 ng/mL, 6.764 ng/mL, 6.102 ng/mL, 5.776 ng/mL and 6.351 ng/mL, respectively.

The binding specificity of the humanized antibodies to human IL-17A was determined by conventional ELISA. The method and procedures are described in Example 8. As shown in FIG. 6, humanized antibodies hu31, hu43, hu44, hu59, hu60 and hu250 specifically bound to IL-17A. The $EC_{50}$ was 8.13 ng/mL, 8.64 ng/mL, 6.76 ng/mL, 6.10 ng/mL, 5.78 ng/mL and 6.35 ng/mL, respectively.

Figure 7:
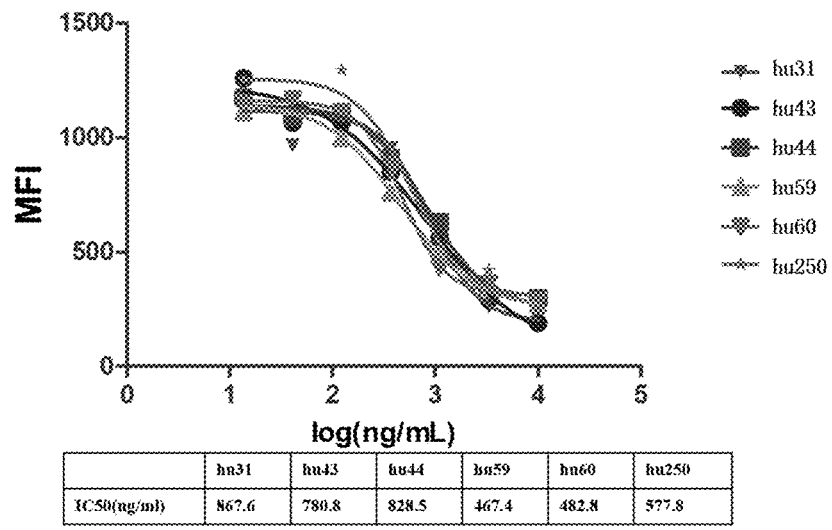
FIG. 7 shows the effect of humanized antibodies on blocking the binding of human IL-17A to IL-17RA on 293F cells assayed by FACS. The antibodies hu31, hu43, hu44, hu59, hu60 and hu250 all block the binding efficiently, with the $IC_{50}$ values being 867.6 ng/mL, 780.8 ng/mL, 828.5 ng/mL, 467.4 ng/mL, 482.8 ng/mL and 577.8 ng/mL, respectively.

Example 12. Blocking of Binding of Human IL-17A to IL-17RA by Humanized Antibodies The blocking of binding of IL-17A to IL-17RA on cells was detected by a competitive cell-based flow cytometry (FACS) assay. The method and procedures are described in Example 9. As shown in FIG. 7, humanized antibodies hu31, hu43, hu44, hu59, hu60 and hu250 significantly inhibited IL-17A from specifically binding to IL-17RA on cells. The $IC_{50}$ was 867.6 ng/mL, 780.8 ng/mL, 828.5 ng/mL, 467.4 ng/mL, 482.8 ng/mL and 577.8 ng/mL, respectively.

Example 13. Antagonism of IL-17A-Induced CXCL1 Expression in Epithelial Cells by Humanized Antibodies IL-17A can stimulate the expression and release of a cytokine CXCL1 in various epithelial cells and other cells. The change in expression level of CXCL1 in cell supernatant can be quantified by ELISA to determine the influence of the humanized antibodies on the bioactivities mediated by IL-17A in the cells.

Figure 8:
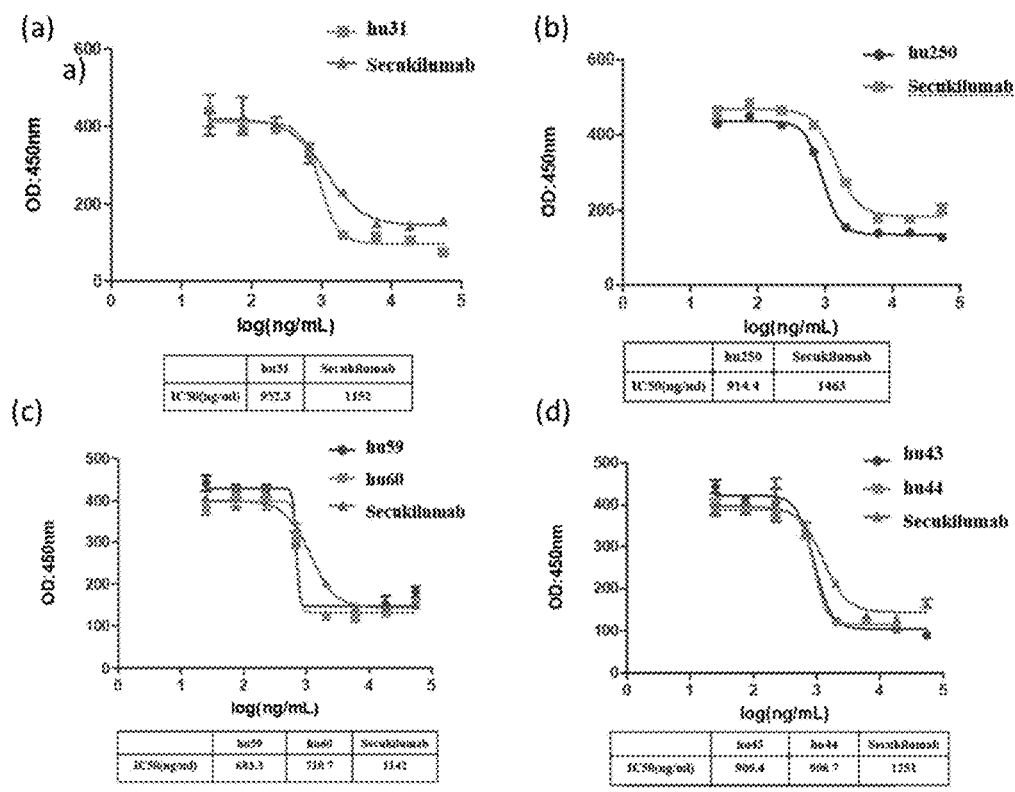
FIG. 8 shows the effect of humanized antibodies on blocking IL-17A-mediated secretion of CXCL1 by epithelial cells assayed by ELISA. The antibodies hu31, hu43, hu44, hu59, hu60 and hu250 all inhibit IL-17A from inducing the expression of CXCL1 in epithelial cells efficiently, and have stronger blocking effect than the control antibody.

HT-29 cells (human colorectal adenocarcinoma epithelial cells, ATCC) were incubated in a culture/assay medium in flasks treated with tissue cultures as per standard techniques. HT-29 grew in tissue cultures-treated flasks until they reached a confluence of 50-80% on the day of the assay. On the day of assay, the cells were washed with PBS and detached from the flask with trypsin+ EDTA to prepare a cell suspension. Dilutions (3-fold serial dilution from 55 µg/mL) of humanized antibodies hu31, hu59, hu60, hu250 or a reference antibody (secukinumab, Novartis) were mixed with human IL-17A (1 µg/mL), transferred to 96-well plates, and incubated for 1 h. 100 µL of suspensions ($2 \times 10^4$ cells) of HT-29 cells (ATCC, human colorectal adenocarcinoma epithelial cells) were added to each well and incubated at 37° C./7% $CO_2$ for 48 h. The cells were centrifuged at 500×g for 5 min, and the supernatant was transferred to new 96-well plates. The CXCL1 expression was determined by an ELISA kit. As shown in FIG. 8, the humanized antibodies hu31, hu59, hu60 and hu250 demonstrated more potent antagonism to IL-17A stimulation of CXCL1 release in epithelial cells than the reference antibody secukinumab.

Example 14. Antagonism of IL-17A-Induced CXCL1 Expression in Mice by Humanized Antibodies The effect of humanized antibodies on IL-17A-mediated bioactivity in vivo was determined by measuring changes in mouse serum CXCL1 levels as described in Example 5. Briefly, 40 female Balb/c mice aged 10 weeks were selected and divided into 8 groups of 5 mice each. 4 days before administration, serum was collected and CXCL1 expression was measured as the baseline. On the day of administration, candidate antibodies (humanized antibodies hu31, hu43, hu44, hu60 and hu250), or an IgG4 isotype control (hIgG) was administered intracardially at a dose of 1 mg/kg. 1 hour after administration, human IL-17A was injected subcutaneously at a dose of 150 µg/kg; 2 hours after the administration of human IL-17A, serum was collected, and the blood CXCL1 concentration was measured and compared with the baseline. The fold change (mean±standard error (mean±SEM)) in CXCL1 concentration before and after administration was calculated for each group. Comparative analysis between the candidate antibodies and the IgG4 isotype control is considered significantly different when P is <0.05 in a Student's t test, *P<0.05, P<0.01, *P<0.001.

Figure 9:
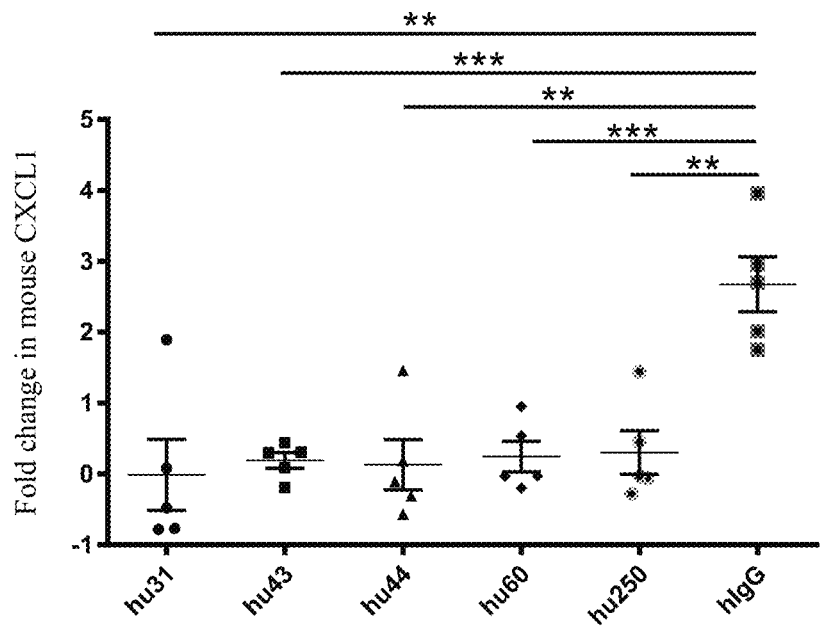
FIG. 9 shows the effect of humanized antibodies on blocking IL-17A-mediated bioactivity in vivo assayed by ELISA. The antibodies hu31, hu43, hu44, hu60 and hu250 inhibit IL-17A from inducing the expression of CXCL1 in mice efficiently, and have stronger blocking effect than the control antibody.

As shown in FIG. 9, the candidate humanized antibodies hu31, hu43, hu44, hu60 and hu250 demonstrated more potent antagonism to IL-17A stimulation of CXCL1 release in epithelial cells than the IgG4 isotype control.

Example 15. Efficacy Study of Humanized Antibodies in Improving the Imiquimod-Induced Psoriasis in Mice Imiquimod administered on the ear and back skins of a mouse can induce psoriasis-like pathological characteristics, including keratinocyte hyperproliferation, inflammatory cell aggregation, dermal papillary vascular hyperplasia and the like, thus constructing a mouse model with psoriasis. The efficacy of the antibodies on mice with psoriasis was determined by endpoints such as clinical scores, ear swelling degrees and the like.

15.1. Methodology

48 C57BL/6 female mice aged 6-8 weeks (purchased from the Model Animal Research Center of Nanjing University, Certificate No. 201605578) were selected. Back hair of the mice was shaved, and the mice other than the sham surgery group were sensitized two days later. Two days before sensitization, the mice were randomized into 5 groups (8 in each): group I was the sham surgery group; group II was PBS group, group III was KLH control group (isotype IgG) receiving KLH; group IV was hu31 treatment group; group V was hu43 treatment group; group VI was hu44 treatment group. The dose for all groups was 50 mg/kg, and the above groups were administered with corresponding drugs intraperitoneally once on day 0 and day 3. On the day of sensitization (day 1), mice in group II-VI were administered with approximately 62.5 mg of imiquimod cream (Aldara, 5%, 3M Health Care Limited) on the right ear and back skins for 4 consecutive days.

15.2. Evaluation

The thickness of the right ear of the mouse was measured daily by a micrometer starting from the day of sensitization. With the ear thickness one day 1 as the baseline, the ear swelling thickness was recorded. The mice were weighed daily, observed for skin scales, induration and erythema, and classified by a 4-score scale: 0, none; 1, mild; 2, moderate; 3, severe; 4, serious. Results were recorded in mean±standard error (mean±SEM). Difference between groups were identified by one-way analysis of variance (ANOVA) and validated by Student's t test, with a P<0.05 indicating significant difference.

Figure 10A:
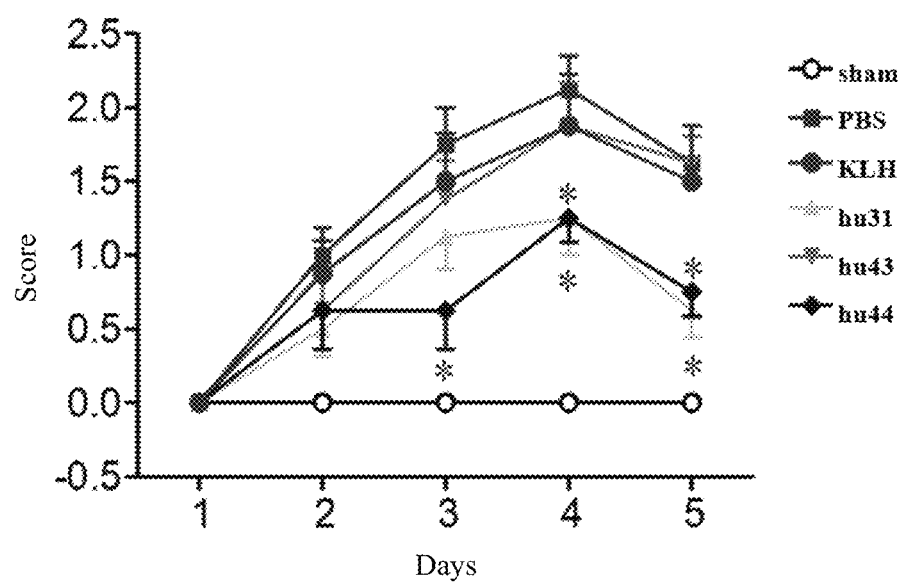
FIG. 10A shows the effect of humanized antibody administration on the clinical score of imiquimod-induced psoriasis in mice. The administration of hu31 and hu44 can significantly inhibit skin scales, induration, swelling and other conditions of inimiquimod-induced psoriasis in the mouse model, i.e., decrease the clinical score (*P<0.05 vs. KLH).
Figure 10B:
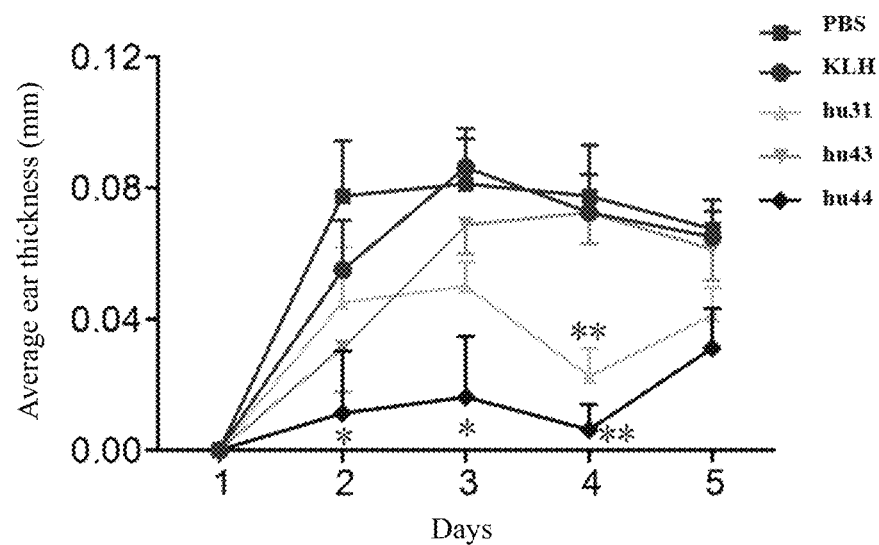
FIG. 10B shows the effect of humanized antibodies on the degree of ear swelling of mice with imiquimod-induced psoriasis. The administration of hu31 and hu44 can significantly improve the degree of ear swelling. (*P<0.05 vs. KLH, **P<0.01 vs. KLH).

As shown in FIG. 10-1, the administration of the candidate antibodies disclosed herein can significantly inhibit skin scales, induration, swelling and other conditions of imiquimod-induced psoriasis in the mouse model, demonstrating decreased scores.

As shown in FIG. 10-2, imiquimod cream administered to mouse right ear from the day of sensitization induced severe swelling and increased ear thickness in the right ear, while the humanized antibody of the present invention significantly improved the ear swelling.

In the mouse model with imiquimod-induced psoriasis, the humanized antibody disclosed herein can obviously resist the morbidity in mice, demonstrating reductions in clinical score of the mice and the ear swelling degree.

Example 16. Efficacy Study of Humanized Antibody in Improving Collagen Type II-Induced Arthritis in Female Cynomolgus Monkey Animals with type II collagen-induced arthritis are models commonly used in studies of rheumatoid arthritis (RA). Such models have similar histopathological features as human RA, and are characterized by inflammation in facet joints and progressive erosion in cartilages and bones. The human/humanized biological macromolecules including antibodies usually have better cross reactivity with antigens from cynomolgus monkey. Thus the cynomolgus monkey model with arthritis is an effective system for analyzing the anti-rheumatism efficacy of the humanized antibody IL-17A disclosed herein. The experiment evaluated the efficacy of the candidate antibodies in a cynomolgus monkey model with arthritis.

16.1. Methodology

Bovine collagen type II (CII, Sichuan University) was dissolved in acetic acid (CAT #10000218; Sinopharm, Shanghai, China), stirred overnight in a 4° C. refrigerator, and emulsified with an equal volume of complete Freund's adjuvant (CAT #F5881, Sigma-Aldrich, USA) to give a collagen emulsion with a final concentration of 2 mg/mL. On day 0, the animals were anesthetized with Zoletil (1.5-5 mg/kg, i.m.), and administered with the collagen emulsion at multiple sites on the back and tail, with 1.5%-5% isoflurane to maintain the anesthetic effect as needed. The animals were re-administered with collagen 3 weeks later (day 21) with the same method as before. The animals were then divided into 4 groups. G1 was normal group without arthritis induction; G2 was vehicle control group; G3 was antibody hu31 treatment group; and G4 was antibody hu59 treatment group. Animals with a score being 5% of the maximum clinical score (192×5%≈10) were sequentially divided into the groups until all animals meeting the requirement were allocated. After the allocation, the treatment was administered at 7.5 mg/kg by infusion pump in 30 minutes, once weekly for 5 weeks.

16.2. Evaluation

Body weight: The body weight of the animals was measured the day before arthritis induction and once weekly thereafter until the end of the study.

Figure 11A:
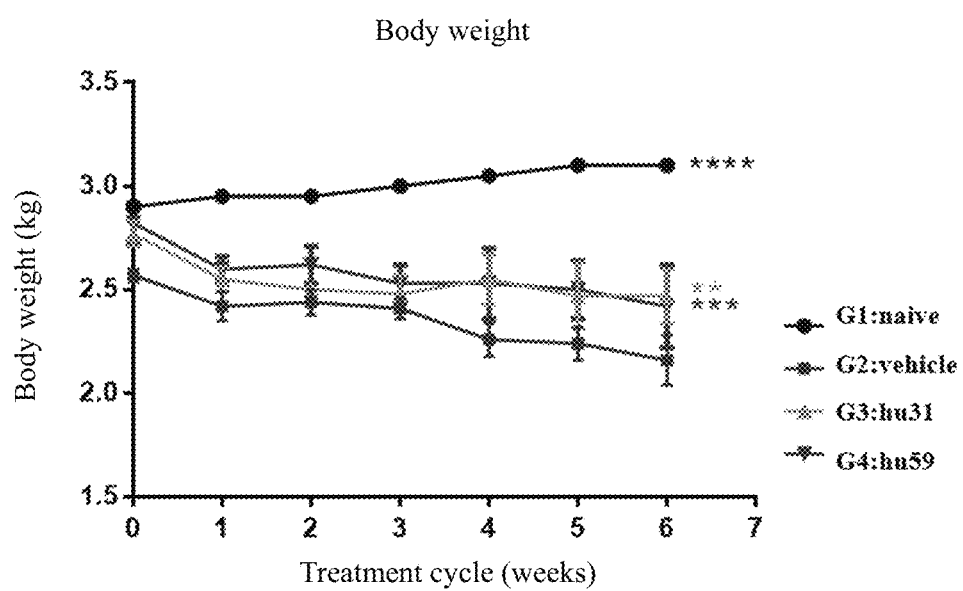
FIG. 11A shows the effect of humanized antibodies on the body weight of female cynomolgus monkeys with type II collagen-induced arthritis. hu31 and hu59 improve the weight loss induced by arthritis to some extent (P<0.01, **P<0.0001, compared with "G2: vehicle group"; One-way ANOVA/Dunnett).
Figure 11B:
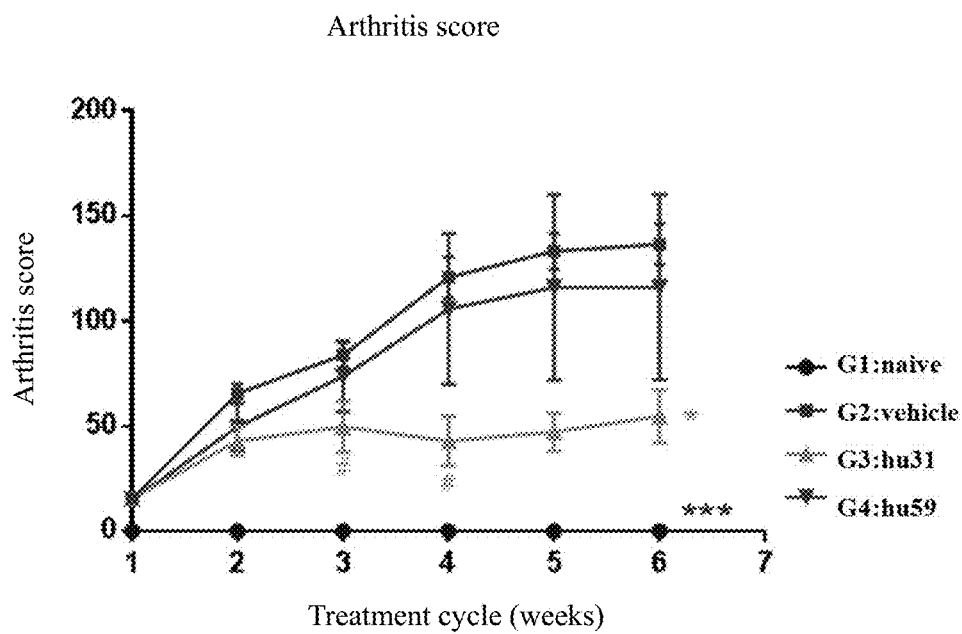
FIG. 11B shows the effect of humanized antibodies on the score of collagen type II-induced arthritis in female cynomolgus monkeys. hu31 significantly inhibits the increasing trend in clinical score of arthritis in cynomolgus monkeys (***P<0.001, #P<0.05, compared with G2: vehicle group; One-way ANOVA/Dunnett).

Arthritis scoring: the monkeys were classified for inflammation on days 0 and 21, and once weekly after day 21 until the end of the study (if early onset occurred, the weekly scoring should start accordingly). The scoring criteria are shown in Table 2. 15 joints in each paw were assessed: 5 metacarpophalangeal joints (MCP), 4 proximal interphalangeal joints (PIP), 5 distal interphalangeal joints (DIP), 1 wrist joint and 1 ankle joint. It is also desirable to assess the severity of lesions in knee/elbow joints in extremities. The sum of the individual joint scores was the arthritis score for the animal, with a maximum score of 192 (16×3×4). Scoring criteria for arthritis: 0, normal; 1, mild arthritis, with slight but distinguishable lesion; 2, moderate swelling; 3, severe arthritis, with severe swelling or obvious joint deformity. Experimental data are presented in mean±standard error (mean±S.E.M). Differences in parameters between vehicle control group, reference drug group and test article group were summarized, with a $p<0.05$ indicating statistically different (One-way ANOVA/Dunnett). As shown in FIG. 11-1, the body weights of cynomolgus monkeys in the normal group (G1) were stable; for the cynomolgus monkeys with induced arthritis, the average weight in the vehicle control group (G2) continuously decreased, and the decreases in monkeys receiving antibodies hu31 and hu59 were controlled. Thus, under the conditions of this study, hu31 and hu59 improve the weight loss caused by arthritis to some extent ($P<0.01$, **$P<0.0001$, compared with "G2: vehicle group"; One-way ANOVA/Dunnett).

As shown in FIG. 11-2, the arthritis clinical scores of animals in normal group remained 0 after allocation; the arthritis score of animals in the vehicle control group (G2) was progressively increased, while the test antibodies hu31 and hu59 significantly inhibited the increasing trend of the arthritis clinical score. Thus, antibodies hu31 and hu59 demonstrated inhibitory effects on the progression of arthritis, and hu31 significantly inhibited the increasing trend in clinical score of arthritis in cynomolgus monkeys (***$P<0.001$, #$P<0.05$, compared with G2: vehicle group; One-way ANOVA/Dunnett).

Figure 12:
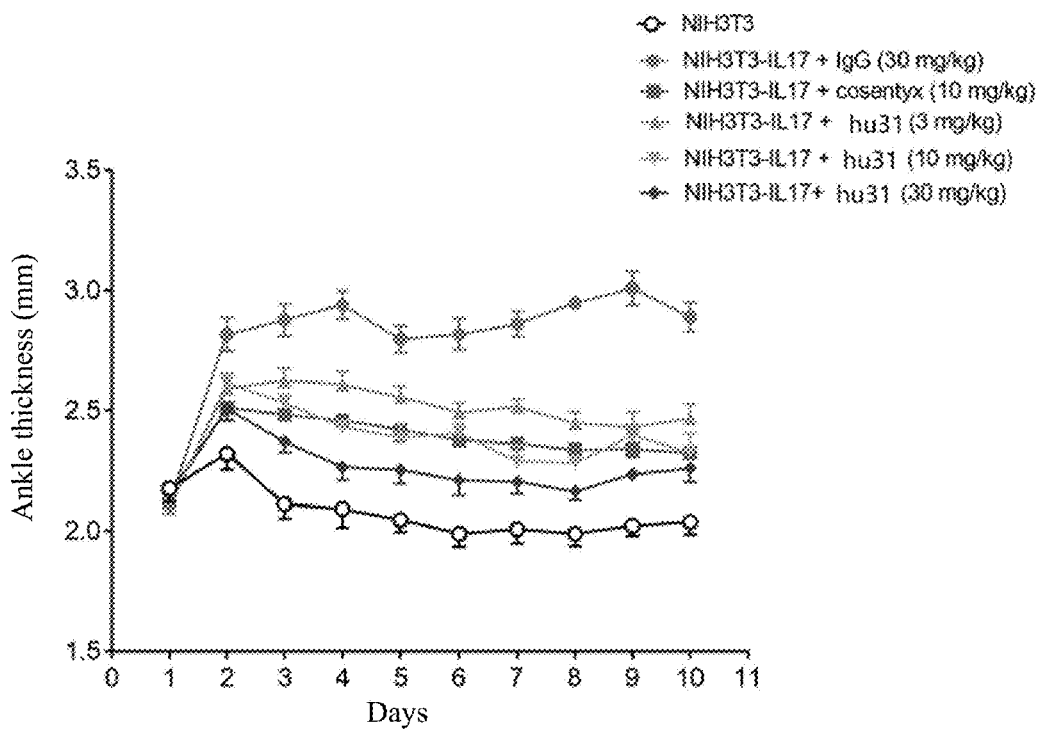
FIG. 12 shows the effect of humanized antibodies on NIH3T3-IL-17 cell-induced joint swelling in mice.

Example 17. Efficacy of Humanized Antibodies on Mouse Joint Swelling Induced by NIH3T3-IL-17 Cells 1. Animals: C57BL/6, female, 6-8 weeks, Beijing Vital River Laboratory Animal Technology Co., Ltd.
2. Cells: NIH3T3 cells, NIH3T3 cells expressing human IL-17.
3. Grouping and dosing regimen:
   NIH3T3 group;
   NIH3T3-IL-17+ reference IgG antibody group (30 mg/kg);
   NIH3T3-IL-17+ treatment antibody high-dose group (hu31, 3 mg/kg);
   NIH3T3-IL-17+ treatment antibody medium-dose group (hu31, 10 mg/kg);
   NIH3T3-IL-17+ treatment antibody low-dose group (hu31, 30 mg/kg);
   NIH3T3-IL-17+ positive drug group (Cosentyx, 10 mg/kg).
4. Modeling and administration:
   NIH3T3-IL-17 cells and NIH3T3 control cells ($2.5×10^5$ cells/mouse, with an injection volume of 25 μL) were injected into the right ankle cavity of the mice.
   Intraperitoneal injections of the antibody hu31 (3, 10, 30 mg/kg) and Cosentyx (10 mg/kg) were given once every 3 days, starting from 1 day before model selection. The efficacy of antibody hu31 injection in the mouse model with arthritis was examined.
5. Detection:
   The ankle thickness was measured by a vernier caliper, and the swelling extent was calculated.
6. Results:
   As shown in FIG. 12, after NIH3T3 cells expressing hIL-17 were injected into the joint cavity of mice, and severe swelling of mice joint was observed the next day.

The swelling inhibition rate was calculated according to the ankle thickness of the mice, wherein the calculation formula is as follows: inhibition rate (%)=(ankle thickness of NIH3T3-IL-17 IgG group—ankle thickness of treatment group)/(ankle thickness of NIH3T3-IL-17 IgG group—ankle thickness of NIH3T3 group)×100. The results showed that, on day 2 after the administration, inhibition of ankle swelling in mice was observed in all treatment groups until the end of study, and a maximum inhibitory effect was observed on day 6 after the administration. On day 10, the inhibition rates of antibody hu31 at 3, 10 and 30 mg/kg were 49.4%, 65.9% and 74.1%, respectively. The inhibition rate of swelling by Cosentyx (10 mg/kg) was 67.1%. The average inhibition rates were calculated on different days in the treatment groups and the results showed that the average inhibition rates were 45.2%, 57.0% and 73.9% for 3, 10 and 30 mg/kg treatment groups, respectively. The average inhibition rate of swelling by Cosentyx (10 mg/kg) was 60.4%. The results suggest that antibody hu31 can inhibit IL-17-induced ankle swelling in mice dose-dependently, and the efficacy at 10 mg/kg is equivalent to that of a positive drug Cosentyx (10 mg/kg). The efficacy at 30 mg/kg is superior to that of the reference drug Cosentyx (10 mg/kg).

Figure 13:
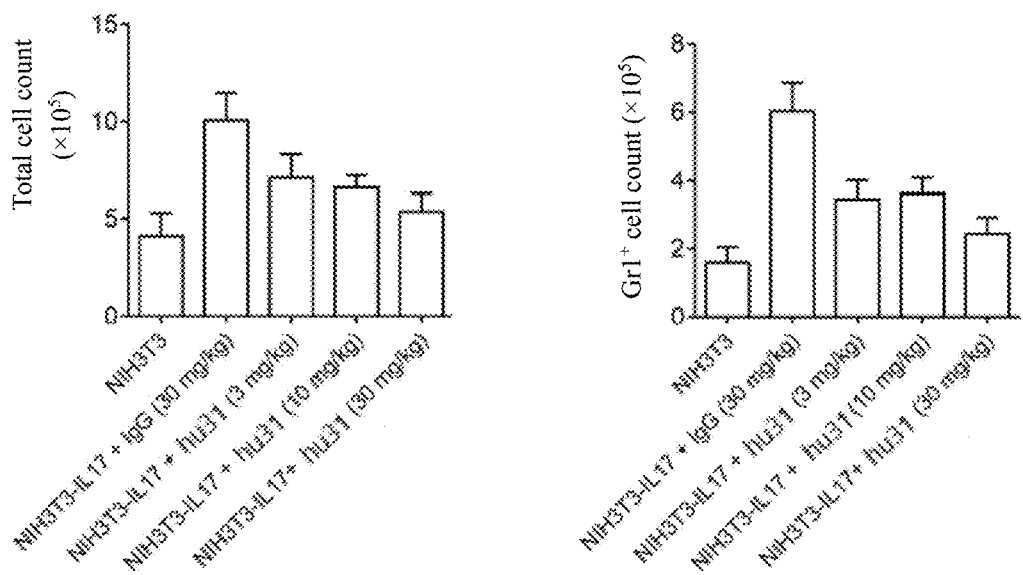
FIG. 13 shows the effect of humanized antibodies in mouse air pouch model of NIH3T3-IL-17 cell-induced inflammation.

Example 18. Efficacy of Humanized Antibodies in Mouse Air Pouch Model of NIH3T3-IL-17 Cell-Induced Inflammation 1. Animals: C57BL/6, male, 6-8 weeks, purchased from Beijing Vital River Laboratory Animal Technology Co., Ltd.
2. Cells: NIH3T3 cells, NIH3T3 cells expressing human IL-17.
3. Reagent: Gr1-FITC antibody, BioLegend
4. Grouping and dosing regimen:
NIH3T3 group
NIH3T3-IL-17+ reference IgG antibody group (30 mg/kg);
NIH3T3-IL-17+ treatment antibody high-dose group (hu31, 30 mg/kg);
NIH3T3-IL-17+ treatment antibody medium-dose group (hu31, 10 mg/kg);
NIH3T3-IL-17+ treatment antibody low-dose group (hu31, 3 mg/kg);
Route of administration: intraperitoneal.
5. Modeling:
Air pouch: The mice were injected with 2.5 mL of air on the back on days 0 and 3. Starting from day 5, cells were injected into the air pouch. Each mouse received $2\times10^5$ cells/500 µL PBS. The mice were allocated into groups each containing 8 mice.
6. Detection:
Leukocytes migrated into the air pouch. Cells in lavage fluid was counted, and the proportion of $Gr1^+$ cells was determined by flow cytometry to calculate the number of neutrophils.
Neutrophil count=total cell count×proportion of $Gr1^+$ cells
7. Results
As shown in FIG. 13, after the mice with air pouch were administered with NIH3T3 cells expressing hIL-17A, as compared with the NIH3T3 group, the number of infiltrating leukocytes in the air pouch of the NIH3T3-IL-17 group significantly increased, and the proportion and number of $Gr1^+$ cells were also significantly elevated, indicating a successful model selection. On the day of modeling, the antibody hu31 (at 3, 10 and 30 mg/kg) was intraperitoneally administered. The inhibition rate was calculated according to the total infiltrating cell count and the $Gr1^+$ cell count, wherein the calculation formula is as follows: inhibition rate (%)=(cell count of NIH3T3-IL-17-IgG group—cell count of treatment group)/(cell count of NIH3T3-IL-17-IgG group—cell count of NIH3T3 group)×100. The results showed that the total infiltrating cell count in the treatment groups of antibody hu31 (3, 10 and 30 mg/kg) was inhibited by 50.0%, 56.7% and 78.3%, respectively. The inhibition rate of the $Gr1^+$ cell count was calculated, demonstrating that: the average $Gr1^+$ cell inhibition rates of all treatment group with antibody hu31 (3, 10 and 30 mg/kg) were 59.1%, 54.5% and 81.8%, respectively. Antibody hu31 can inhibit IL-17 induced total cell infiltration and inflammatory cell infiltration in mice in a dose-dependent manner.

The invention claimed is:

1. An antibody or an antigen-binding fragment thereof that specifically binds to IL-17A, comprising a heavy chain variable region (VH) comprising HCDR1, HCDR2 and HCDR3; and a light chain variable region (VL) comprising LCDR1, LCDR2 and LCDR3; wherein amino acid sequences of the HCDR1, the HCDR2 and the HCDR3 comprise SEQ ID NO: 1, SEQ ID NO: 2 and SEQ ID NO: 3, respectively, and amino acid sequences of the LCDR1, the LCDR2 and the LCDR3 comprise SEQ ID NO: 13, SEQ ID NO: 14 and SEQ ID NO: 15, respectively; or amino acid sequences of the HCDR1, the HCDR2 and the HCDR3 comprise SEQ ID NO: 1, SEQ ID NO: 2 and SEQ ID NO: 3, respectively, and amino acid sequences of the LCDR1, the LCDR2 and the LCDR3 comprises SEQ ID NO: 16, SEQ ID NO: 17 and SEQ ID NO: 18, respectively; or amino acid sequences of the HCDR1, the HCDR2 and the HCDR3 comprise SEQ ID NO: 4, SEQ ID NO: 5 and SEQ ID NO: 6, respectively, and amino acid sequences of the LCDR1, the LCDR2 and the LCDR3 comprise SEQ ID NO: 19, SEQ ID NO: 20 and SEQ ID NO: 21, respectively; or amino acid sequences of the HCDR1, the HCDR2 and the HCDR3 comprise SEQ ID NO: 7, SEQ ID NO: 8 and SEQ ID NO: 9, respectively, and amino acid sequences of the LCDR1, the LCDR2 and the LCDR3 comprise SEQ ID NO: 22, SEQ ID NO: 23 and SEQ ID NO: 24, respectively; or amino acid sequences of the HCDR1, the HCDR2 and the HCDR3 comprise SEQ ID NO: 10, SEQ ID NO: 11 and SEQ ID NO: 12, respectively, and amino acid sequences of the LCDR1, the LCDR2 and the LCDR3 comprise SEQ ID NO: 22, SEQ ID NO: 23 and SEQ ID NO: 24, respectively; or amino acid sequences of the HCDR1, the HCDR2 and the HCDR3 comprise SEQ ID NO: 60, SEQ ID NO: 61 and SEQ ID NO: 62, respectively, and amino acid sequences of the LCDR1, the LCDR2 and the LCDR3 comprise SEQ ID NO: 63, SEQ ID NO: 64 and SEQ ID NO: 65, respectively.

2. The antibody or the antigen-binding fragment thereof according to claim 1 comprising a heavy chain variable region (VH) having an amino acid sequence selected from SEQ ID NOs: 25, 26, 27, 28, 33, 35, 37 and 40, and a light chain variable region (VL) having an amino acid sequence selected from SEQ ID NOs: 29, 30, 31, 32, 34, 36, 38, 39 and 41.

3. The antibody or the antigen-binding fragment thereof according to claim 1, wherein the heavy chain variable region comprises SEQ ID NO: 25, and the light chain variable region comprises SEQ ID NO: 29 or 30; or the heavy chain variable region comprises SEQ ID NO: 26, and the light chain variable region comprises SEQ ID NO: 31; or the heavy chain variable region comprises SEQ ID NO: 27 or 28, and the light chain variable region comprises SEQ ID NO: 32; or the heavy chain variable region comprises SEQ ID NO: 33 or 35, and the light chain variable region comprises SEQ ID NO: 34; or the heavy chain variable region comprises SEQ ID NO: 35, and the light chain variable region comprises SEQ ID NO: 36; or the heavy chain variable region comprises SEQ ID NO: 37, and the light chain variable region comprises SEQ ID NO: 38 or 39; or the heavy chain variable region comprises SEQ ID NO: 40, and the light chain variable region comprises SEQ ID NO: 41.

4. The antibody or the antigen-binding fragment thereof according to claim 1, wherein the antibody or the antigen-binding fragment thereof is a murine antibody, a chimeric antibody, or a humanized antibody.

5. The antibody or the antigen-binding fragment thereof according to claim 1, wherein the antibody is an intact antibody and the antigen-binding fragment is selected from a single chain antibody, an Fab antibody, an Fab' antibody, an (Fab') 2 antibody, a bispecific antibody and a multispecific antibody.

6. The antibody or the antigen-binding fragment thereof according to claim 1, wherein the antibody or the antigen-binding fragment thereof is of an IgG1, IgG2, IgG3 or IgG4 type.

7. The antibody or the antigen-binding fragment thereof according to claim 1, comprising a heavy chain (HC) having an amino acid sequence selected from SEQ ID NOs: 42, 44, 46 and 49, and a light chain (LC) having an amino acid sequence selected from SEQ ID NOs: 43, 45, 47, 48 and 50.

8. The antibody or the antigen-binding fragment thereof according to claim 7, wherein
   the light chain has an amino acid sequence set forth in SEQ ID No: 43 and the heavy chain has an amino acid sequence set forth in SEQ ID No: 42 or 44; or
   the light chain has an amino acid sequence set forth in SEQ ID No: 45 and the heavy chain has an amino acid sequence set forth in SEQ ID No: 44; or
   the light chain has an amino acid sequence set forth in SEQ ID No: 47 or 48 and the heavy chain has an amino acid sequence set forth in SEQ ID No: 46; or
   the light chain has an amino acid sequence set forth in SEQ ID No: 50 and the heavy chain has an amino acid sequence set forth in SEQ ID No: 49.

9. An isolated nucleic acid molecule or isolated nucleic acid molecules encoding the antibody or the antigen-binding fragment thereof according to claim 1.

10. The isolated nucleic acid molecule or the isolated nucleic acid molecules of claim 9, wherein the isolated nucleic acid molecules are selected from the group consisting of SEQ ID NOs: 51 and 52, SEQ ID NOs: 53 and 52, SEQ ID NOs: 53 and 54, SEQ ID NOs: 55 and 56, SEQ ID NOs: 55 and 57, and SEQ ID NOs: 58 and 59.

11. An expression vector or a recombinant vector comprising the isolated nucleic acid molecule or the isolated nucleic acid molecules according to claim 9.

12. A host cell transformed with the expression vector or the recombinant vector according to claim 11.

13. A pharmaceutical composition, comprising
   (i) the antibody or the antigen-binding fragment thereof according to claim 1, a nucleic acid molecule or nucleic acid molecules encoding the antibody or the antigen-binding fragment thereof, a vector comprising the nucleic acid molecule or the nucleic acid molecules; or
   (ii) a host cell comprising the nucleic acid molecule or the nucleic acid molecules or the vector; and
   a pharmaceutically acceptable carrier or excipient.

14. A method for preventing or treating a disease or a disorder diseases or disorders mediated by IL-17A, comprising administering to a subject in need of a therapeutically effective amount of
   (i) the antibody or the antigen-binding a functional fragment thereof of claim 1; or
   (ii) a nucleic acid molecule or nucleic acid molecules encoding the antibody or the antigen-binding functional fragment thereof, or a vector comprising the nucleic acid molecule or the nucleic acid molecules; or
   (iii) a pharmaceutical composition comprising the antibody or the antigen-binding functional fragment thereof, the nucleic acid molecule or the nucleic acid molecules, or the expression vector.

15. The method of claim 14, wherein the disease is arthritis, rheumatoid arthritis, psoriasis, ankylosing spondylitis, chronic obstructive pulmonary disease, systemic lupus erythematosus (SLE), lupus nephritis, asthma, multiple sclerosis or cystic fibrosis.

* * * * *